United States Patent
Machida et al.

(10) Patent No.: US 7,932,083 B2
(45) Date of Patent: Apr. 26, 2011

(54) DNA PARTICIPATING IN HYDROXYLATION OF MACROLIDE COMPOUND

(75) Inventors: Kazuhiro Machida, Shizuoka (JP); Takashi Nakashima, Kanagawa (JP); Yasuhide Aritoku, Shizuoka (JP); Toshio Tsuchida, Shizuoka (JP)

(73) Assignees: Mercian Corporation, Tokyo (JP); Eisai R&D Management Co., Ltd., Tokyo (JP)

( * ) Notice: Subject to any disclaimer, the term of this patent is extended or adjusted under 35 U.S.C. 154(b) by 365 days.

(21) Appl. No.: 10/577,655

(22) PCT Filed: Nov. 25, 2004

(86) PCT No.: PCT/JP2004/017906
§ 371 (c)(1),
(2), (4) Date: May 1, 2006

(87) PCT Pub. No.: WO2005/052152
PCT Pub. Date: Jun. 9, 2005

(65) Prior Publication Data
US 2008/0070286 A1 Mar. 20, 2008

(30) Foreign Application Priority Data

Nov. 27, 2003 (JP) .............................. 2003-396828

(51) Int. Cl.
*C12N 5/00* (2006.01)
*C12N 15/00* (2006.01)
*C12P 21/06* (2006.01)
*C07H 21/02* (2006.01)
*C07H 21/04* (2006.01)

(52) U.S. Cl. .................. 435/325; 435/69.1; 435/320.1; 536/23.1; 536/23.2; 536/23.7

(58) Field of Classification Search .................. None
See application file for complete search history.

(56) References Cited

U.S. PATENT DOCUMENTS

| | | | |
|---|---|---|---|
| 5,824,513 A | 10/1998 | Katz et al. | |
| 6,004,787 A | 12/1999 | Katz et al. | |
| 6,503,737 B1 | 1/2003 | Reeves et al. | |
| 7,026,352 B1 | 4/2006 | Mizui et al. | |
| 7,375,088 B2 | 5/2008 | Bachmann et al. | |
| 2004/0266008 A1 | 12/2004 | Bachmann et al. | |
| 2005/0084859 A1* | 4/2005 | Nakajima et al. | 435/6 |
| 2005/0245514 A1 | 11/2005 | Kotake et al. | |
| 2006/0234337 A1 | 10/2006 | Arisawa et al. | |
| 2006/0235002 A1 | 10/2006 | Nagai et al. | |
| 2009/0269820 A1 | 10/2009 | Machida et al. | |

FOREIGN PATENT DOCUMENTS

| | | |
|---|---|---|
| CA | 2 463 855 A1 | 5/2003 |
| CA | 2 494 536 A1 | 2/2004 |
| CA | 2 507 641 A1 | 6/2004 |
| CN | 1489583 A | 4/2004 |
| EP | 1 380 579 A1 | 1/2004 |

(Continued)

OTHER PUBLICATIONS

Hyun Chang-Gu et al.; An Efficient Approach for Cloning P450 Hydroxylase Genes From Actinomycetes; Journal of Microbiology and Biotechnology, Korean Society for Applied Microbiology, vol. 8, No. 3, Jun. 1, 1998, pp. 295-299.

(Continued)

*Primary Examiner* — Janet L. Epps-Smith
(74) *Attorney, Agent, or Firm* — Birch, Stewart, Kolasch & Birch, LLP

(57) ABSTRACT

The present invention provides a DNA participating in biological transformation of a macrolide compound 11107B. The present invention provides, particularly, a DNA participating in biological transformation of a macrolide compound 11107B represented by the formula (I) into a 16-position hydroxy macrolide compound 11107D represented by the formula (II), the DNA encoding a protein having 16-position hydroxylating enzymatic activity or ferredoxin, to a method of isolating the DNA, to a protein encoded by the DNA, a plasmid carrying the DNA, a transformant obtained by transforming using the plasmid and a method of producing a 16-position hydroxy compound by using the transformant.

(I)

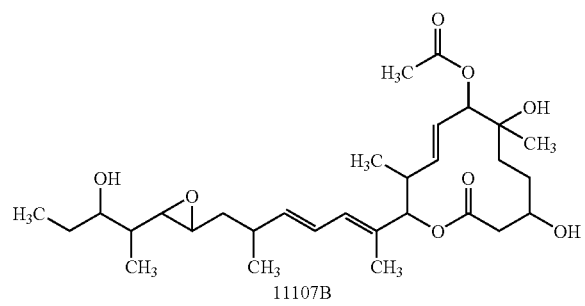

11107B (II)

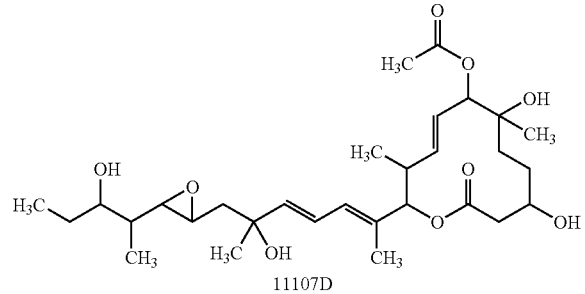

11107D

10 Claims, No Drawings

FOREIGN PATENT DOCUMENTS

| | | |
|---|---|---|
| EP | 1 457 558 A1 | 9/2004 |
| EP | 1 500 704 A1 | 1/2005 |
| EP | 1 508 570 A1 | 2/2005 |
| EP | 1 541 570 A1 | 6/2005 |
| EP | 1 705 247 A1 | 9/2006 |
| WO | WO-93/12236 A1 | 6/1993 |
| WO | WO 93/13663 A1 | 7/1993 |
| WO | WO-02/060890 A1 | 8/2002 |
| WO | WO-02/092801 A2 | 11/2002 |
| WO | WO-03/040370 A1 | 5/2003 |
| WO | WO03/040370 A1 * | 5/2003 |
| WO | WO03040370 A1 * | 5/2003 |
| WO | WO-03/087381 A1 | 10/2003 |
| WO | WO-03/099813 A1 | 12/2003 |
| WO | WO-2004/011459 A1 | 2/2004 |
| WO | WO-2004/011661 A1 | 2/2004 |
| WO | WO-2004/050890 A1 | 6/2004 |
| WO | WO-2004/061116 A2 | 7/2004 |
| WO | WO 2004/065401 A1 | 8/2004 |
| WO | WO 2005/052152 A1 | 6/2005 |
| WO | WO 2006/009276 A1 | 1/2006 |

OTHER PUBLICATIONS

Kazuhiro Machida et al., "Increase in Pladienolide D Production Rate Using a Streptomyces Strain Overexpressing a Cytochrome P450 Gene", Journal of Bioscience and Bioengineering, vol. 105, No. 6, pp. 649-654 (2008).

European Patent Office Action issued Dec. 21, 2009 in Application No. 04 799 902.4-2405, pp. 1-4.

Chang-Gu Hyun et al.; An Efficient Approach for Cloning P450 Hydroxylase Genes From Actinomycetes; Journal of Microbiology and Biotechnology, Korean Society for Applied Microbiology, vol. 8, No. 3, Jun. 1, 1998, pp. 295-299.

"Cell Technology," vol. 14, No. 5, pp. 591-593, 1995.

Beck et al., "Nucleotide sequence of bacteriophage fd DNA," Nucleic Acids Research, vol. 5, No. 12, pp. 4495-4503, Dec. 1978.

Bibb et al., "Genetic Studies of the Fertility Plasmid SCP2* Variants in Streptomyces coelicolor A3(2)," Journal of General Microbiology, vol. 126, pp. 427-442, 1981.

Bibb et al., "Nucleotide sequences encoding and promoting expression of three antibiotic resistance genes indigenous to Streptomyces," Mol. Gen. Genet., vol. 199, pp. 26-36, 1985.

Bibb et al., "The mRNA for the 23S rRNA methylase encoded by the ermE gene of Saccharopolyspora erythraea is translated in the absense of a conventional ribosome-binding site," Molecular Microbiology, vol. 14, No. 3, pp. 533-545, 1994.

Chater, "Streptomyces Phages and Their Applications to Streptomyces Genetics," the Bacteria, vol. IX, Chapter 5, pp. 119-158, 1986.

Chinese Office Action, dated Feb. 5, 2010, for Chinese Application No. 2006800182893.

Decker et al., "Cloning and Characterization of a Polyketide Synthase Gene from Streptomyces fradiae Tü2717, Which Carries the Genes for Biosynthesis of the Angucycline Antibiotic Urdamycin A . . . ," Journal of Bacteriology, vol. 177, No. 21, pp. 6126-6136, Nov. 1995.

Donadio et al., "An erythromycin analog produced by reprogramming of polyketide synthesis," Proc. Natl. Acad. Sci. USA, vol. 90, pp. 7119-7123, Aug. 1993.

Guilhot et al., "Efficient Transposition in Mycobacteria: Construction of Mycobacterium smegmatis Insertional Mutant Libraries," Journal of Bacteriology, vol. 176, No. 2, pp. 535-539, Jan. 1994.

Hopwood et al., "Molecular Genetics of Polyketides and its Comparison to Fatty Acid Biosynthesis," Annu. Rev. Genet., vol. 24, pp. 37-66, 1990.

Katz et al., "Polyketide Synthesis: Prospects for Hybrid Antibiotics," Annu. Rev. Microbiol., vol. 47, pp. 875-912, 1993.

Kendall et al., "Complete Nucleotide Sequence of the Streptomyces lividans Plasmid pIJ101 and Correlation of the Sequence with Genetic Properties," Journal of Bacteriology, vol. 170, No. 10, pp. 4634-4651, Oct. 1988.

Kojima et al., "The rpoZ Gene, Encoding the RNA Polymerase Omega Subunit, Is Required for Antibiotic Production and Morphological Differentiation in Streptomyces kasugaensis," Journal of Bacteriology, vol. 184, No. 23, pp. 6417-6423, Dec. 2002.

Lamb et al., "The Cytochrome P450 Complement (CYPome) of Streptomyces coelicolor A3(2)*," The Journal of Biological Chemistry, vol. 277, No. 27, pp. 24000-24005, Jul. 5, 2002.

Lampel et al., "Cloning and Sequencing of a Gene Encoding a Novel Extracellular Neutral Proteinase from Streptomyces sp. Strain C5 and Expression of the Gene in Streptomyces lividans 1326," Journal of Bacteriology, vol. 174, No. 9, pp. 2797-2808, May 1992.

McAlpine et al., "Microbial Genomics as a Guide to Drug Discovery and Structural Elucidation: ECO-02301, a Novel Antifungal Agent, as an Example," J. Natl. Prod., vol. 68, pp. 493-496, 2005.

McDaniel et al., "Multiple genetic modifications of the erythromycin polyketide synthase to produce a library of novel "unnatural" natural products," Proc. Natl. Acad. Sci. USA, vol. 96, pp. 1846-1851, Mar. 1999.

Neal et al., "Nucleotide sequence analysis reveals similarities between proteins determining methylenomycin A resistance in Streptomyces and tetracycline resistance in eubacteria," Gene, vol. 58, pp. 229-241, 1987.

Pfeifer et al., "Biosynthesis of Complex Polyketides in a Metabolically Engineered Strain of E. coli," Science, vol. 291, pp. 1790-1792, Mar. 2, 2001.

Sakai et al., "Pladienolides, New Substances from Culture of Streptomyces platensis Mer-11107. I. Taxonomy, fermentation, isolation and screening," The Journal of Antibiotics, vol. 57, No. 3, pp. 173-179, XP-002462515, Mar. 2004.

Schmid et al., "AUD4, a new amplifiable element from Streptomyces lividans," Microbiology, vol. 145, pp. 3331-3341, 1999.

Schwecke, et al., "The biosynthetic gene cluster for the polyketide immunosuppressant rapamycin," Proc. Natl. Acad. Sci. USA, vol. 92, pp. 7839-7843, XP 000652288, Aug. 1995.

Seki-Asano et al., "Isolation and Characterzation of a New 12-Membered Macrolide FD-895," The Journal of Antibiotics, vol. 47, No. 12, pp. 1395-1401, XP-002951021, 1994.

Shah et al., "Cloning, Characterization and Heterologous Expression of a Polyketide Synthase and P-450 Oxidase Involved in the Biosynthesis of the Antibiotic Oleandomycin," The Journal of Antibiotics, vol. 53, No. 5, pp. 502-508, May 2000.

Takano et al., "Construction of thiostrepton-inducible, high-copy-number expression vectors for use in Streptomyces spp," Gene, vol. 166, Issue 1, pp. 133-137, Dec. 1, 1995.

Triglia et al., "A procedure for in vitro amplification of DNA segments that lie outside the boundaries of known sequences," Nucleic Acids Research, vol. 16, No. 18, p. 8186, 1988.

US Office Action, dated Aug. 24, 2010, for U.S. Appl. No. 11/919,579.

US Office Action, dated Dec. 9, 2010, for U.S. Appl. No. 11/919,579.

US Office Action, dated Feb. 1, 2010, for U.S. Appl. No. 11/630,689.

US Office Action, dated May 25, 2010, for U.S. Appl. No. 11/630,689.

US Office Action, dated Oct. 20, 2010, for U.S. Appl. No. 11/630,689.

Weber et al., "An Erythromycin Derivative Produced by Targeted Gene Disruption in Saccharopolyspora erythraea," Science, vol. 252, pp. 114-117, Apr. 5, 1991.

Xue et al., "A gene cluster for macrolide antibiotic biosynthesis in Streptomyces venezuelae: Architecture of metabolic diversity," Proc. Natl. Acad. Sci. USA, vol. 95, pp. 12111-12116, Oct. 1998.

Yanisch-Perron et al., "Improved M13 phage cloning vectors and host strains: nucleotide sequences of the M13mp18 and pUC19 vectors," Gene, vol. 33, Issue 1, pp. 103-119, 1985.

Yiguang, "Application of Genetic Engineering Techniques in the Study of Macrolide Antibiotics," Institute of Medicinal Biotechnology, Chinese Academy of Medical Sciences & Peking Union Medical College, vol. 18, No. 2, pp. 92-98, Mar. 31, 1997.

Zalacain et al., "Nucleotide sequence of the hygromycin B phosphotransferase gene from Streptomyces hygroscopicus," Nucleic Acids Research, vol. 14, No. 4, pp. 1565-1581, 1986.

* cited by examiner

SEQUENCE LISTING

```
<160> NUMBER OF SEQ ID NOS: 25

<210> SEQ ID NO 1
<211> LENGTH: 3793
<212> TYPE: DNA
<213> ORGANISM: Streptomyces sp.
<220> FEATURE:
<221> NAME/KEY: CDS
<222> LOCATION: (1322)..(2548)
<220> FEATURE:
<221> NAME/KEY: CDS
<222> LOCATION: (2564)..(2761)

<400> SEQUENCE: 1
ctgcagctcg acgtgcgggt cggacttcac gttgaagtac cagaccggat gcttgggcgc      60
accgcccagc gaggcgaccg ccgcgtaact ccccctcgtgc tcgacccgca tcagcggcgt     120
cttgcggatc tttccgctgc gcgcgccccg ggtggtgagc acgatgaccg gcagcccggt     180
gtcccgcagc gtggtgccct tggtgccccc ggaactctcg tacagctcga cctgctcgcg     240
cacccactgc gtcgggctgg gctcgtactc gccctcaagt ggcaagggat ccgtctcctt     300
cgtcggtccg gcggatggtg ctccggacg tcccaactcc cgcggccgcc cggatcatcc     360
gtaccgcatg cccccttcgcc cgagcgggtg atcaccgttc cggccatccg gtcgtccgca     420
ccgcgagcac caggatcacg gcgctggaga gcagggccgt gaccagccgc ccccggtggc     480
ccgtcagggc gcgacccagc agcgcgcccc cgcccgccag cagtagctgc cagctcgcgg     540
acgcggcgaa ggccgccgcg gcgaacaccg cccgttcag cggccgtgcc gcaccggcgg     600
cgccgctgcc gagcaccagc gccacgaagt agaccaccgt catgggattg agcagggtga     660
tcccgagaag gccgagataa gccctgccg cgcctggaac cggccgttcc gggcgggtgg     720
tgagccgatg ggcgcggtac tgccgcaggg cgagcagcgc cgcccgcagc gcgagcaccg     780
cgaggaccag cgccgaggcc cagcgcagcg ggtccagcac cggccgcagc tgtgccgcga     840
gggcggcgcc gcccacggtc gcgagcagcg cgtacagccc gtcggccgtg gcgacgccga     900
gcgccgccga ggcgccggtg cgcagcgagg tgcgggcggt gagggagacc agataggtcc     960
cgaccgcgcc gacgggcacc gcgatgccgt acccggcgag caggcccgcg agcagcgcgc    1020
ccgtcacggg cgtgcggac tggttcctcc ggggacggcg gggctgctgt cggcccggca    1080 ccgcggggc ggtggcagcg ggcgtcggca ggagggaggc tgtaggaggc atgggccgat    1140
cctggggccg ccgcgcccgc accggcaaat gaattacggc gcgttccagc ccccggccgg    1200
ctcgctcttc ggccacttca ccgcgtacgg cgatctggcc gaacttgctg tcgcccata    1260 ggtgcctcgg gcatctaatg aagatcggca cgacgcacct cttcgtctgc gaggtcttc    1320 c atg acg gaa ctg acg gac atc acc ggc ccg ggg acc ccg gcc gaa ccc    1369
    Met Thr Glu Leu Thr Asp Ile Thr Gly Pro Gly Thr Pro Ala Glu Pro
```

-continued

| | 1 | | | 5 | | | | 10 | | | | 15 | | | |
|---|---|---|---|---|---|---|---|---|---|---|---|---|---|---|---|

```
gtc gca ttc ccc cag gac cgc acc tgc ccc tac cac ccc ccc acc gga      1417
Val Ala Phe Pro Gln Asp Arg Thr Cys Pro Tyr His Pro Pro Thr Gly
             20                  25                  30 tac ggc ccg ctg cgc gac ggg cgc agc ctg tcc cgc gtc acc ctc ttc      1465
Tyr Gly Pro Leu Arg Asp Gly Arg Ser Leu Ser Arg Val Thr Leu Phe
         35                  40                  45 gac ggc cgc gag gtc tgg atg gtc acg ggc cac gcc acc gcc cgc gcg      1513
Asp Gly Arg Glu Val Trp Met Val Thr Gly His Ala Thr Ala Arg Ala
 50                  55                  60 ctg ctc gcg gac ccc cgg ctg tcc acc gac cgc acc ctc ccg ggc ttc      1561
Leu Leu Ala Asp Pro Arg Leu Ser Thr Asp Arg Thr Leu Pro Gly Phe
65                  70                  75                  80 ccc gtg ccc acg gcc cgc ttc gcg gcc gtc cgc gac cgg cgg gtg gcg      1609
Pro Val Pro Thr Ala Arg Phe Ala Ala Val Arg Asp Arg Arg Val Ala
                 85                  90                  95 ctg ctc ggc gtg gac gac ccg gtc cac cag acc cag cgg cgg atg atg      1657
Leu Leu Gly Val Asp Asp Pro Val His Gln Thr Gln Arg Arg Met Met
             100                 105                 110 atc ccg tcg ttc acc ctc aag cgc gcg gcc ggg ctg cgg ccc acc atc      1705
Ile Pro Ser Phe Thr Leu Lys Arg Ala Ala Gly Leu Arg Pro Thr Ile
         115                 120                 125 cag cgg acc gtc gac ggg ctg ctg gac gcg atg atc gag aag ggg ccg      1753
Gln Arg Thr Val Asp Gly Leu Leu Asp Ala Met Ile Glu Lys Gly Pro
130                 135                 140 ccg gcc gag ctg gtc tcc gcc ttc gcc ctg ccc gtg ccc tcg gtg gtc      1801
Pro Ala Glu Leu Val Ser Ala Phe Ala Leu Pro Val Pro Ser Val Val
145                 150                 155                 160 atc tgc ggc ctg ctc ggc gtg ccg tac gcc gac cac gag ttc ttc gag      1849
Ile Cys Gly Leu Leu Gly Val Pro Tyr Ala Asp His Glu Phe Phe Glu
                 165                 170                 175 gaa cag tcc cgc acg ctg ctg cgc ggt ccc acg gcc gcc gac tcg caa      1897
Glu Gln Ser Arg Thr Leu Leu Arg Gly Pro Thr Ala Ala Asp Ser Gln
             180                 185                 190 ggg gcg cgc gag cgg ctc gag gag tac ctc ggc ggg ctg atc gac gac      1945
Gly Ala Arg Glu Arg Leu Glu Glu Tyr Leu Gly Gly Leu Ile Asp Asp
         195                 200                 205 aag gag cgg cag gcc gaa ccc ggc gac ggc gtc ctg gac gac ctc gtc      1993
Lys Glu Arg Gln Ala Glu Pro Gly Asp Gly Val Leu Asp Asp Leu Val
210                 215                 220 cac cag cgg ctg cgc acc ggc gag ctg gac cgg cgc gac gtg gtg gcg      2041
His Gln Arg Leu Arg Thr Gly Glu Leu Asp Arg Arg Asp Val Val Ala
225                 230                 235                 240 ctg gcc gtc atc ctg ctc gtg gcc ggg cac gag acg acc gcc aac atg      2089
Leu Ala Val Ile Leu Leu Val Ala Gly His Glu Thr Thr Ala Asn Met
                 245                 250                 255 atc tcc ctc ggc acc tac acg ctg ctg cgg cac ccc ggc cgg ctg gcc      2137
Ile Ser Leu Gly Thr Tyr Thr Leu Leu Arg His Pro Gly Arg Leu Ala
             260                 265                 270 gag ctg cgc gcc gac ccg gcg ctg ctg ccc gcc gtg gag gag ctg          2185
Glu Leu Arg Ala Asp Pro Ala Leu Leu Pro Ala Val Glu Glu Leu
         275                 280                 285 atg cgg atg ctc tcg atc gcg gac ggg ctg ctg cgc ctg gcc ctg gag      2233
Met Arg Met Leu Ser Ile Ala Asp Gly Leu Leu Arg Leu Ala Leu Glu
290                 295                 300 gac atc gag atc gcc ggc gcc acg atc cgg gcc ggc gag ggc gtc ctg      2281
Asp Ile Glu Ile Ala Gly Ala Thr Ile Arg Ala Gly Glu Gly Val Leu
305                 310                 315                 320 ttc tcc acc tcg ctg atc aac cgc gac gag tcc gtg ttc gac gac ccc      2329
Phe Ser Thr Ser Leu Ile Asn Arg Asp Glu Ser Val Phe Asp Asp Pro
```

```
                             325                 330                 335
gac acc ctg gac ttc cac cgc tcc acc cgc cac cac gtg gcc ttc ggt        2377
Asp Thr Leu Asp Phe His Arg Ser Thr Arg His His Val Ala Phe Gly
                340                 345                 350 ttc ggc atc cac cag tgc ctg ggc cag aac ctg gcc cgc gcc gag ctg        2425
Phe Gly Ile His Gln Cys Leu Gly Gln Asn Leu Ala Arg Ala Glu Leu
                355                 360                 365 gag atc gcc ctg ggc acg ctc ctg gag cgg ctc ccc ggc ctc cgg ctg        2473
Glu Ile Ala Leu Gly Thr Leu Leu Glu Arg Leu Pro Gly Leu Arg Leu
            370                 375                 380 gcc gcg ccc gcc gag gag atc ccg ttc aaa ccc ggc gac acg atc cag        2521
Ala Ala Pro Ala Glu Glu Ile Pro Phe Lys Pro Gly Asp Thr Ile Gln
385                 390                 395                 400 ggg atg ctg gaa ctc ccc gtg acc tgg taagaggctc tggtc atg cac atc       2572
Gly Met Leu Glu Leu Pro Val Thr Trp                  Met His Ile
                405                                      410 gac atc gac aag gac cgc tgc atc ggc gcc ggc cag tgc gcg ctg gcc        2620
Asp Ile Asp Lys Asp Arg Cys Ile Gly Ala Gly Gln Cys Ala Leu Ala
                415                 420                 425 gcc ccg ggc gtg ttc acc cag gac gac gac ggc tac agc acc ctg ctc        2668
Ala Pro Gly Val Phe Thr Gln Asp Asp Asp Gly Tyr Ser Thr Leu Leu
            430                 435                 440 ccc ggc cgc gag gac ggg ggg gac ccg atg gtc cgg gag gcg gcc            2716
Pro Gly Arg Glu Asp Gly Gly Asp Pro Met Val Arg Glu Ala Ala
445                 450                 455                 460 cgc gcc tgc ccg gtg agc gcc atc cgg gtg acc gaa ccg gcc ggc            2761
Arg Ala Cys Pro Val Ser Ala Ile Arg Val Thr Glu Pro Ala Gly
                465                 470                 475 tgaggcgggg ccggcggcc gcggcccgct gccgggaccg ccgttcccag ttcagtaggg       2821
tcgtgcgatg acctcacagg ccgggaagcc cttcctctac gtcgtcgtct gcgcggccgg     2881
gaccgccgcc ggagtcacca cgctgatcgg cgccgcccag gcgcggggct gggaggtggg    2941
ggtcctggcc acgccggtgg cgatgggcgg gttcttcgac acggctgcgg tcgaggagat    3001
gacgggccgg cccatccgct cggcctggcg ctcgccggcc gatccgcgcc cgttcccgcc    3061
gccgggcgcc gtggtggtgg cgcccgccac cttcaacacc gtcaacaagt gggcggccgg    3121
tctcgccgac acgctcgccg tcggcacgct ctgcgaggcg gcgggcctcg gcgtgccgat    3181
cgccgtcctg ccctgcgtgg cggacgcgct ggccgcccac cccgcgtacc gggagggcct    3241
tctccggctg cgtgggatgg gcgtccgctt cggcgagccg tacgccggcc gccggggga    3301 ggacggcgag gcggacggcg cacggccggg gttcgcctgg gagaacgccc tggacctgct    3361
ggagcgggcc tgaacccgct ccccgacccg tagggcctgt ctgacactgt cagacaggcc    3421
ctaacggcag gtcagcgccg gcccggccag catgccgccg gtgtagaggt cctggccccg    3481
cggcagccag tagcccagcc tggagaccac cgtggagcag tcaggcccga cggtgacgcg    3541
gaccttcacc gtctcgggac ggccgggctg cagcgcggtc agcgcgcagt ccagggagta    3601
cgcgagccgg gtcttcgagg taccggccga ccagcgggtt gacgcagcgg cgtcgtccg    3661 tggcgatccg caccccggtg cccgccccgc cgatgagtcc gagccgggcg ctgccgtcgc    3721
cctcgtcgct gtcccggcgg accgtgtagg tcagcgtggt ggtggcgtcg cgccgcaggg    3781
tgtccggtcg ac                                                        3793

<210> SEQ ID NO 2
<211> LENGTH: 409
<212> TYPE: PRT
<213> ORGANISM: Streptomyces sp.
```

<400> SEQUENCE: 2

```
Met Thr Glu Leu Thr Asp Ile Thr Gly Pro Gly Thr Pro Ala Glu Pro
1               5                   10                  15

Val Ala Phe Pro Gln Asp Arg Thr Cys Pro Tyr His Pro Thr Gly
            20                  25                  30

Tyr Gly Pro Leu Arg Asp Gly Arg Ser Leu Ser Arg Val Thr Leu Phe
                35                  40                  45

Asp Gly Arg Glu Val Trp Met Val Thr Gly His Ala Thr Ala Arg Ala
    50                  55                  60

Leu Leu Ala Asp Pro Arg Leu Ser Thr Asp Arg Thr Leu Pro Gly Phe
65                  70                  75                  80

Pro Val Pro Thr Ala Arg Phe Ala Ala Val Arg Asp Arg Val Ala
                85                  90                  95

Leu Leu Gly Val Asp Asp Pro Val His Gln Thr Gln Arg Arg Met Met
                100                 105                 110

Ile Pro Ser Phe Thr Leu Lys Arg Ala Ala Gly Leu Arg Pro Thr Ile
            115                 120                 125

Gln Arg Thr Val Asp Gly Leu Leu Asp Ala Met Ile Glu Lys Gly Pro
    130                 135                 140

Pro Ala Glu Leu Val Ser Ala Phe Ala Leu Pro Val Pro Ser Val Val
145                 150                 155                 160

Ile Cys Gly Leu Leu Gly Val Pro Tyr Ala Asp His Glu Phe Phe Glu
                165                 170                 175

Glu Gln Ser Arg Thr Leu Leu Arg Gly Pro Thr Ala Ala Asp Ser Gln
            180                 185                 190

Gly Ala Arg Glu Arg Leu Glu Glu Tyr Leu Gly Gly Leu Ile Asp Asp
    195                 200                 205

Lys Glu Arg Gln Ala Glu Pro Gly Asp Gly Val Leu Asp Asp Leu Val
210                 215                 220

His Gln Arg Leu Arg Thr Gly Glu Leu Asp Arg Arg Asp Val Val Ala
225                 230                 235                 240

Leu Ala Val Ile Leu Leu Val Ala Gly His Glu Thr Thr Ala Asn Met
                245                 250                 255

Ile Ser Leu Gly Thr Tyr Thr Leu Leu Arg His Pro Gly Arg Leu Ala
            260                 265                 270

Glu Leu Arg Ala Asp Pro Ala Leu Pro Ala Ala Val Glu Glu Leu
    275                 280                 285

Met Arg Met Leu Ser Ile Ala Asp Gly Leu Leu Arg Leu Ala Leu Glu
290                 295                 300

Asp Ile Glu Ile Ala Gly Ala Thr Ile Arg Ala Gly Glu Gly Val Leu
305                 310                 315                 320

Phe Ser Thr Ser Leu Ile Asn Arg Asp Glu Ser Val Phe Asp Asp Pro
                325                 330                 335

Asp Thr Leu Asp Phe His Arg Ser Thr Arg His His Val Ala Phe Gly
            340                 345                 350

Phe Gly Ile His Gln Cys Leu Gly Gln Asn Leu Ala Arg Ala Glu Leu
    355                 360                 365

Glu Ile Ala Leu Gly Thr Leu Leu Glu Arg Leu Pro Gly Leu Arg Leu
370                 375                 380

Ala Ala Pro Ala Glu Glu Ile Pro Phe Lys Pro Gly Asp Thr Ile Gln
385                 390                 395                 400

Gly Met Leu Glu Leu Pro Val Thr Trp
                405
```

```
<210> SEQ ID NO 3
<211> LENGTH: 66
<212> TYPE: PRT
<213> ORGANISM: Streptomyces sp.

<400> SEQUENCE: 3

Met His Ile Asp Ile Asp Lys Asp Arg Cys Ile Gly Ala Gly Gln Cys
1               5                   10                  15

Ala Leu Ala Ala Pro Gly Val Phe Thr Gln Asp Asp Gly Tyr Ser
            20                  25                  30

Thr Leu Leu Pro Gly Arg Glu Asp Gly Gly Asp Pro Met Val Arg
        35                  40                  45

Glu Ala Ala Arg Ala Cys Pro Val Ser Ala Ile Arg Val Thr Glu Pro
50                  55                  60

Ala Gly
65

<210> SEQ ID NO 4
<211> LENGTH: 2329
<212> TYPE: DNA
<213> ORGANISM: Streptomyces sp.
<220> FEATURE:
<221> NAME/KEY: CDS
<222> LOCATION: (420)..(1604)
<220> FEATURE:
<221> NAME/KEY: CDS
<222> LOCATION: (1643)..(1834)

<400> SEQUENCE: 4
ggatccacgg gtggccgccg cgctcgcccg ggtgaccgac cggcgtatcg gctatgtcgc      60
cgcgctcttc gcggcgctgg gcttccccga gggcgaggcg cgggaccgcg gcctgctggc     120
gtacaccgcc tacctcggcc acaccagct cggacatgcc gtccgacaga gcctgccggc      180
cgaggcggca cacgaccgct atctggatgg cgtgatcgac accctcgtac ggccgcggga     240
cggaggcgat gaagccgaac atgtcacaat ctgaacgagg ttggcggaac tgcgcgcaga     300
acatgcccgg tatccgcggc atgaggtgag atcggcgcgg cgaaacacgg tgcgccacag     360
cgttgccatc tcacacacga gcaactcgag ccacttgaga ctcgtacggg aggaaattc     419 gtg acc gaa gcc atc ccc tac ttt cag aac cgc acc tgt ccc tac cac     467
Val Thr Glu Ala Ile Pro Tyr Phe Gln Asn Arg Thr Cys Pro Tyr His
1               5                   10                  15 ccg ccc gcc gcc tat cag cca ctg cgc ggg gcc ggc ccg ctg agc cat     515
Pro Pro Ala Ala Tyr Gln Pro Leu Arg Gly Ala Gly Pro Leu Ser His
            20                  25                  30 gtc acg ttc tac gac ggc cgg aag gtg tgg gcg gtc acc ggc cac ccc     563
Val Thr Phe Tyr Asp Gly Arg Lys Val Trp Ala Val Thr Gly His Pro
        35                  40                  45 gag gca cgg gcg ctg ctg acc gac cag cga ctc tcc gcc gac cgg cag     611
Glu Ala Arg Ala Leu Leu Thr Asp Gln Arg Leu Ser Ala Asp Arg Gln
50                  55                  60 aac ccg gcc ttc ccg gtc ccc ttc gaa cgc ttc gcg gcc atc cgc cgg     659
Asn Pro Ala Phe Pro Val Pro Phe Glu Arg Phe Ala Ala Ile Arg Arg
65                  70                  75                  80 gtc cgg acg ccg ctg atc ggg gtc gac gac ccg gag cac aac acc cag     707
Val Arg Thr Pro Leu Ile Gly Val Asp Asp Pro Glu His Asn Thr Gln
                85                  90                  95 cgc cgg atg ctg atc ccc agc ttc agc ctc aag cgg acc gcc gca ctg     755
Arg Arg Met Leu Ile Pro Ser Phe Ser Leu Lys Arg Thr Ala Ala Leu
            100                 105                 110 cgg ccg gag atc cag cgg atc gtc gac ggg ctg ctc gac cgg atg ctg     803
```

```
                Arg Pro Glu Ile Gln Arg Ile Val Asp Gly Leu Leu Asp Arg Met Leu
                            115                 120                 125 gat cag ggc ccg ccc acc gag ctg gtc tcc gcg ttc gcc ctg ccg gtc        851
Asp Gln Gly Pro Pro Thr Glu Leu Val Ser Ala Phe Ala Leu Pro Val
        130                 135                 140 ccg tcg atg gtg atc tgc gca ctg ctc gga gtc tca tac gcc gac cat        899
Pro Ser Met Val Ile Cys Ala Leu Leu Gly Val Ser Tyr Ala Asp His
145                 150                 155                 160 gag ttc ttc gag gag gag tcc cgc cgc atc ctg cgc ggc cgg tcg gcc        947
Glu Phe Phe Glu Glu Glu Ser Arg Arg Ile Leu Arg Gly Arg Ser Ala
                165                 170                 175 gag gag gcg gag gac gcc cgg ctg aag ctg gag gag tac ttc acc ggg        995
Glu Glu Ala Glu Asp Ala Arg Leu Lys Leu Glu Glu Tyr Phe Thr Gly
            180                 185                 190 ctg atc gcc gcc aag gag aag aac ccg ggc gac ggg ctg ctg gac gag       1043
Leu Ile Ala Ala Lys Glu Lys Asn Pro Gly Asp Gly Leu Leu Asp Glu
                195                 200                 205 ctg atc gag gac cgg ctg cgg acc ggc gcg ctc acc cgc gac gag ctg       1091
Leu Ile Glu Asp Arg Leu Arg Thr Gly Ala Leu Thr Arg Asp Glu Leu
        210                 215                 220 gtc cgg ctc gcc atg atc ctg ctg gtg gcc ggc cat gag acc acc gcc       1139
Val Arg Leu Ala Met Ile Leu Leu Val Ala Gly His Glu Thr Thr Ala
225                 230                 235                 240 aac atg atc tcg ctc ggc acc ttc acc ctg ctg gac cac ccc gag cag       1187
Asn Met Ile Ser Leu Gly Thr Phe Thr Leu Leu Asp His Pro Glu Gln
                245                 250                 255 ctg gcg cag ctc aag gcc gac gag ggc ctg atg ccg gcc gcc atc gag       1235
Leu Ala Gln Leu Lys Ala Asp Glu Gly Leu Met Pro Ala Ala Ile Glu
            260                 265                 270 gag ctg ctg cga ttc ctg tcc atc gcg gac ggc ctg ctg cgg gtg gcg       1283
Glu Leu Leu Arg Phe Leu Ser Ile Ala Asp Gly Leu Leu Arg Val Ala
        275                 280                 285 acg gag gac atc gag atc ggc ggt cag gtg atc cgg gcc gac gac gcg       1331
Thr Glu Asp Ile Glu Ile Gly Gly Gln Val Ile Arg Ala Asp Asp Ala
290                 295                 300 gtc ctg ttc ccc gcc tca ctg atc aac cgg gac gag gcc gcc tat ccg       1379
Val Leu Phe Pro Ala Ser Leu Ile Asn Arg Asp Glu Ala Ala Tyr Pro
305                 310                 315                 320 gca ccc gac gag ctg gac ctc ggc cgt tcg gcc cgc cat cac gtg gcg       1427
Ala Pro Asp Glu Leu Asp Leu Gly Arg Ser Ala Arg His His Val Ala
                325                 330                 335 tcc ggc ttc ggg atc cac cag tgc ctg ggg cag aac ctc gcc cgc gcg       1475
Ser Gly Phe Gly Ile His Gln Cys Leu Gly Gln Asn Leu Ala Arg Ala
            340                 345                 350 gag atg gag atc gcg ctg cgc tca ctg ttc acc agg atc ccg cag ctg       1523
Glu Met Glu Ile Ala Leu Arg Ser Leu Phe Thr Arg Ile Pro Gln Leu
        355                 360                 365 cgg ctc gcc gtg ccg gcc gcc gag att ccg ttc aag gac gga gac acc       1571
Arg Leu Ala Val Pro Ala Ala Glu Ile Pro Phe Lys Asp Gly Asp Thr
370                 375                 380 ctg caa ggc atg atc gaa ctg ccg ctg gcc tgg tagcagccag gacggcagac     1624
Leu Gln Gly Met Ile Glu Leu Pro Leu Ala Trp
385                 390                 395 caaagaaagg ggtccgga atg cgg atc gcg atc gac acc gac cgc tgt atc       1675
                    Met Arg Ile Ala Ile Asp Thr Asp Arg Cys Ile
                                        400                 405 ggc gcc ggc cag tgt gcc ctg acc gcg ccc ggg ggt ttc acc cag gat       1723
Gly Ala Gly Gln Cys Ala Leu Thr Ala Pro Gly Gly Phe Thr Gln Asp
            410                 415                 420 gac gac ggt ttc agt gca ctg ctg ccc ggc cgg gag gac ggc gcc ggc       1771
```

```
Asp Asp Gly Phe Ser Ala Leu Leu Pro Gly Arg Glu Asp Gly Ala Gly
            425                 430                 435 gac ccg ctg gtg cgg gaa gcc gcc cgc gcc tgc ccc gtg cag gcc att      1819
Asp Pro Leu Val Arg Glu Ala Ala Arg Ala Cys Pro Val Gln Ala Ile
        440                 445                 450 gcg gtc acc gac gat tagcagcacc cccgcggacg acccggcaga cgcgcgcggc      1874
Ala Val Thr Asp Asp
455 cccggctgac acccggcgcc cgaggcgcgc ccgagccgtc cgcccctcca cttgtcccta    1934 cggcatccac cccatccgct accgcaacac cccttgggtg acgggcagtt tcgaggaccc    1994 cggtgtgccc ggggcgtact ggtgaccgtc accggcttca cgccgcgatt gcccacatag    2054 gcgtcgtcgc tcgcggcgat cacgaagcgc ggtcggtgcc ccggctcgta acggtgcacg    2114 atgcccggca gttccacggt gaaccgccgg ccacatcgg gcacccgggc cggggccacc     2174 aacaggtgca ccagcgtctt cctgccgttc ggcgcgacat cgtagagctt ggcgaacagc    2234 accagcttgt ccgccgcatc cgcggaccgc tgcgcccgcc cggcctgcgg cgaggcaacc    2294 ttcagcgtca ccctcggcgc gcccaccacg tcgac                              2329

<210> SEQ ID NO 5
<211> LENGTH: 395
<212> TYPE: PRT
<213> ORGANISM: Streptomyces sp.

<400> SEQUENCE: 5

Val Thr Glu Ala Ile Pro Tyr Phe Gln Asn Arg Thr Cys Pro Tyr His
1               5                   10                  15

Pro Pro Ala Ala Tyr Gln Pro Leu Arg Gly Ala Gly Pro Leu Ser His
            20                  25                  30

Val Thr Phe Tyr Asp Gly Arg Lys Val Trp Ala Val Thr Gly His Pro
        35                  40                  45

Glu Ala Arg Ala Leu Leu Thr Asp Gln Arg Leu Ser Ala Asp Arg Gln
    50                  55                  60

Asn Pro Ala Phe Pro Val Pro Phe Glu Arg Phe Ala Ala Ile Arg Arg
65                  70                  75                  80

Val Arg Thr Pro Leu Ile Gly Val Asp Asp Pro Glu His Asn Thr Gln
                85                  90                  95

Arg Arg Met Leu Ile Pro Ser Phe Ser Leu Lys Arg Thr Ala Ala Leu
            100                 105                 110

Arg Pro Glu Ile Gln Arg Ile Val Asp Gly Leu Leu Asp Arg Met Leu
        115                 120                 125

Asp Gln Gly Pro Pro Thr Glu Leu Val Ser Ala Phe Ala Leu Pro Val
    130                 135                 140

Pro Ser Met Val Ile Cys Ala Leu Leu Gly Val Ser Tyr Ala Asp His
145                 150                 155                 160

Glu Phe Phe Glu Glu Ser Arg Arg Ile Leu Arg Gly Arg Ser Ala
                165                 170                 175

Glu Glu Ala Glu Asp Ala Arg Leu Lys Leu Glu Glu Tyr Phe Thr Gly
            180                 185                 190

Leu Ile Ala Ala Lys Glu Lys Asn Pro Gly Asp Gly Leu Leu Asp Glu
        195                 200                 205

Leu Ile Glu Asp Arg Leu Arg Thr Gly Ala Leu Thr Arg Asp Glu Leu
    210                 215                 220

Val Arg Leu Ala Met Ile Leu Leu Val Ala Gly His Glu Thr Thr Ala
225                 230                 235                 240
```

```
Asn Met Ile Ser Leu Gly Thr Phe Thr Leu Leu Asp His Pro Glu Gln
                245                 250                 255

Leu Ala Gln Leu Lys Ala Asp Glu Gly Leu Met Pro Ala Ala Ile Glu
            260                 265                 270

Glu Leu Leu Arg Phe Leu Ser Ile Ala Asp Gly Leu Leu Arg Val Ala
        275                 280                 285

Thr Glu Asp Ile Glu Ile Gly Gly Gln Val Ile Arg Ala Asp Ala
    290                 295                 300

Val Leu Phe Pro Ala Ser Leu Ile Asn Arg Asp Glu Ala Ala Tyr Pro
305                 310                 315                 320

Ala Pro Asp Glu Leu Asp Leu Gly Arg Ser Ala Arg His His Val Ala
            325                 330                 335

Ser Gly Phe Gly Ile His Gln Cys Leu Gly Gln Asn Leu Ala Arg Ala
        340                 345                 350

Glu Met Glu Ile Ala Leu Arg Ser Leu Phe Thr Arg Ile Pro Gln Leu
    355                 360                 365

Arg Leu Ala Val Pro Ala Ala Glu Ile Pro Phe Lys Asp Gly Asp Thr
370                 375                 380

Leu Gln Gly Met Ile Glu Leu Pro Leu Ala Trp
385                 390                 395

<210> SEQ ID NO 6
<211> LENGTH: 64
<212> TYPE: PRT
<213> ORGANISM: Streptomyces sp.

<400> SEQUENCE: 6

Met Arg Ile Ala Ile Asp Thr Asp Arg Cys Ile Gly Ala Gly Gln Cys
1               5                   10                  15

Ala Leu Thr Ala Pro Gly Gly Phe Thr Gln Asp Asp Gly Phe Ser
            20                  25                  30

Ala Leu Leu Pro Gly Arg Glu Asp Gly Ala Gly Asp Pro Leu Val Arg
        35                  40                  45

Glu Ala Ala Arg Ala Cys Pro Val Gln Ala Ile Ala Val Thr Asp Asp
    50                  55                  60

<210> SEQ ID NO 7
<211> LENGTH: 1860
<212> TYPE: DNA
<213> ORGANISM: Unknown
<220> FEATURE:
<223> OTHER INFORMATION: Description of Unknown Sequence: nucleotide
      sequence with coding region derived from an unknown source
<220> FEATURE:
<221> NAME/KEY: CDS
<222> LOCATION: (172)..(1383)
<220> FEATURE:
<221> NAME/KEY: CDS
<222> LOCATION: (1399)..(1593)

<400> SEQUENCE: 7
cggggatcgt acgccgtacc gtttcggggc aaccgaatta cgatgcggaa tggatggttc    60
ccagccagat cccgcaggta gccgatctgg ccgaacttga tgtcgtgcac tggatgcctc   120
gggcatctaa tgaagatcgg cacgacgcat ccttcgtctg cgaggtctcc c atg aca   177
                                                         Met Thr
                                                           1 gac acg aca gac ctg acc gag ctg tca gat ccc gtc tcc ttc ccc cag   225
Asp Thr Thr Asp Leu Thr Glu Leu Ser Asp Pro Val Ser Phe Pro Gln
        5                   10                  15 gac cgg agc tgc ccc tac cac ccg ccc acc ggg tac gac ccg ctg cgc   273
```

```
Asp Arg Ser Cys Pro Tyr His Pro Pro Thr Gly Tyr Asp Pro Leu Arg
    20                  25                  30 acc gaa cgg ccg ccc gcc cgc atc cgg ctc tac gac ggc cgc ccc gcc      321
Thr Glu Arg Pro Pro Ala Arg Ile Arg Leu Tyr Asp Gly Arg Pro Ala
 35                  40                  45                  50 tgg ctc gtc acc ggc cac gcc gtc gcc cgt gac ctg ctg gtc gac ccc      369
Trp Leu Val Thr Gly His Ala Val Ala Arg Asp Leu Leu Val Asp Pro
                 55                  60                  65 cgc ctg tcc acg gac cgc acc cgc tcg ggc ttc ccg gcc aca act ccc      417
Arg Leu Ser Thr Asp Arg Thr Arg Ser Gly Phe Pro Ala Thr Thr Pro
                     70                  75                  80 cgc ttc gcc gcg gtc cgc gac cgc aag ccg gcg ctc ctc ggc gtc gac      465
Arg Phe Ala Ala Val Arg Asp Arg Lys Pro Ala Leu Leu Gly Val Asp
             85                  90                  95 gac ccc aag cac cgc acc cag cgg tgg atg atg atc ccg agc ttc acc      513
Asp Pro Lys His Arg Thr Gln Arg Trp Met Met Ile Pro Ser Phe Thr
        100                 105                 110 ctc agg cgc gcc acc gag ctc agg ccg cgc atc cag gag atc gtc gac      561
Leu Arg Arg Ala Thr Glu Leu Arg Pro Arg Ile Gln Glu Ile Val Asp
115                 120                 125                 130 gaa ctg ctg gac gtg atg atc gcc cag gga ccc ccg gcc gac ctg gtg      609
Glu Leu Leu Asp Val Met Ile Ala Gln Gly Pro Pro Ala Asp Leu Val
                    135                 140                 145 cgt tcc ttc gcg ctg ccg gtg ccg tcc atg gtg atc tgc gcc ctg ctc      657
Arg Ser Phe Ala Leu Pro Val Pro Ser Met Val Ile Cys Ala Leu Leu
                150                 155                 160 ggc gtg ccc tac gcc gac cac gag ttc ttc gag gac cag tcc agg cgg      705
Gly Val Pro Tyr Ala Asp His Glu Phe Phe Glu Asp Gln Ser Arg Arg
            165                 170                 175 ctg ctg cgc gga ccg gcg gcc gag gac acg cag gac gcc cgg gac cgg      753
Leu Leu Arg Gly Pro Ala Ala Glu Asp Thr Gln Asp Ala Arg Asp Arg
        180                 185                 190 ctc gcc gcg tac ctg gag gac ctg atc gac gag aag cgg cgc cgg ccc      801
Leu Ala Ala Tyr Leu Glu Asp Leu Ile Asp Glu Lys Arg Arg Arg Pro
195                 200                 205                 210 ggt gac ggc ctg ctg gac gaa ctc gtc cag cag cgt ctg aac gaa ggc      849
Gly Asp Gly Leu Leu Asp Glu Leu Val Gln Gln Arg Leu Asn Glu Gly
                    215                 220                 225 gag ctc gac cgg gag gaa ctg acc gcg ctg gcg atg atc ctg ctg gtc      897
Glu Leu Asp Arg Glu Glu Leu Thr Ala Leu Ala Met Ile Leu Leu Val
                230                 235                 240 gcg ggc cac gag acc acc gcc aac atg atc tcc ctg ggc acc tac acg      945
Ala Gly His Glu Thr Thr Ala Asn Met Ile Ser Leu Gly Thr Tyr Thr
            245                 250                 255 ctc ctg ctg cac ccc gaa cgg ctg acc gag ctg cgc gcc gac ccc gcg      993
Leu Leu Leu His Pro Glu Arg Leu Thr Glu Leu Arg Ala Asp Pro Ala
        260                 265                 270 ctg ctg ccg gcc gcc gtc gag gaa ctg atg cgg atg ctg tcc atc gcg     1041
Leu Leu Pro Ala Ala Val Glu Glu Leu Met Arg Met Leu Ser Ile Ala
275                 280                 285                 290 gac gga ctg ctg cgg cag gcc acc gag gac atc gag atc gcc ggg acc     1089
Asp Gly Leu Leu Arg Gln Ala Thr Glu Asp Ile Glu Ile Ala Gly Thr
                    295                 300                 305 acc atc agg gcc ggg gac ggc gtg gtc ttc tcc acc tct gtc atc aac     1137
Thr Ile Arg Ala Gly Asp Gly Val Val Phe Ser Thr Ser Val Ile Asn
                310                 315                 320 cgc gac gag gac gtc tac ccg gcc ccc gac acc ctc gac ttc cac cgc     1185
Arg Asp Glu Asp Val Tyr Pro Ala Pro Asp Thr Leu Asp Phe His Arg
            325                 330                 335 tcg acc cgc cac cac gtc gcc ttc ggt ttc gga atc cac cag tgc ctc     1233
```

```
                Ser Thr Arg His His Val Ala Phe Gly Phe Gly Ile His Gln Cys Leu
                        340                 345                 350 ggc cag aac ctc gcc cgc acc gaa ctg gag atc gcc ctg cgc acg ctc          1281
Gly Gln Asn Leu Ala Arg Thr Glu Leu Glu Ile Ala Leu Arg Thr Leu
355                 360                 365                 370 ctc gaa cgg ctg ccc acg ctc cgg ctc gcc gcc cca ccg gag gaa atc          1329
Leu Glu Arg Leu Pro Thr Leu Arg Leu Ala Ala Pro Pro Glu Glu Ile
                375                 380                 385 ccc ttc aaa ccc ggc gac acc atc cag ggg atg ctg gaa ctc ccc gtc          1377
Pro Phe Lys Pro Gly Asp Thr Ile Gln Gly Met Leu Glu Leu Pro Val
            390                 395                 400 agc tgg taagaggctg ccgtc atg cat atc gag atc gac aag gac cgc tgc         1428
Ser Trp                 Met His Ile Glu Ile Asp Lys Asp Arg Cys
                                405                 410 atc ggc gcc gga cag tgc gcc ctg acc gcc ccg ggt gtg ttc acc cag          1476
Ile Gly Ala Gly Gln Cys Ala Leu Thr Ala Pro Gly Val Phe Thr Gln
415                 420                 425                 430 gac gac gac ggc ttc agt gac ctg ttg ccc ggc cgg gag gac ggc gcc          1524
Asp Asp Asp Gly Phe Ser Asp Leu Leu Pro Gly Arg Glu Asp Gly Ala
                435                 440                 445 ggc gac ccg atg gtc cgg gag gcc gcc agg gcc tgc ccc gtg agt gcc          1572
Gly Asp Pro Met Val Arg Glu Ala Ala Arg Ala Cys Pro Val Ser Ala
            450                 455                 460 atc acg ctg tcc gag gac ggg taggggccg agccgcgccg cccgccggtc              1623
Ile Thr Leu Ser Glu Asp Gly
                465 cgctgccgcg gcgccgtgcc gacgcggcgg ccggccggcc cgtccggtgc ccgtcgcgtc        1683 gccccgtggc cccggcggcg gctgattgac tagggttccc gggtgagcga acaggcccag        1743 aagccctccg gggcgccgcc cgcgaaagac accgggacgg cgcccgggaa acccctttcct       1803 ctacgtcgtc gtctgcgccg ccggcatcgc cgaaggcgtc agcaagctga tcaccgc           1860

<210> SEQ ID NO 8
<211> LENGTH: 404
<212> TYPE: PRT
<213> ORGANISM: Unknown
<220> FEATURE:
<223> OTHER INFORMATION: Derived from an unknown source

<400> SEQUENCE: 8

Met Thr Asp Thr Thr Asp Leu Thr Glu Leu Ser Asp Pro Val Ser Phe
1               5                   10                  15

Pro Gln Asp Arg Ser Cys Pro Tyr His Pro Pro Thr Gly Tyr Asp Pro
            20                  25                  30

Leu Arg Thr Glu Arg Pro Pro Ala Arg Ile Arg Leu Tyr Asp Gly Arg
        35                  40                  45

Pro Ala Trp Leu Val Thr Gly His Ala Val Ala Arg Asp Leu Leu Val
    50                  55                  60

Asp Pro Arg Leu Ser Thr Asp Thr Arg Ser Gly Phe Pro Ala Thr
65                  70                  75                  80

Thr Pro Arg Phe Ala Ala Val Arg Asp Arg Lys Pro Ala Leu Leu Gly
                85                  90                  95

Val Asp Asp Pro Lys His Arg Thr Gln Arg Trp Met Met Ile Pro Ser
            100                 105                 110

Phe Thr Leu Arg Arg Ala Thr Glu Leu Arg Pro Arg Ile Gln Glu Ile
        115                 120                 125

Val Asp Glu Leu Leu Asp Val Met Ile Ala Gln Gly Pro Pro Ala Asp
    130                 135                 140
```

-continued

```
Leu Val Arg Ser Phe Ala Leu Pro Val Pro Ser Met Val Ile Cys Ala
145                 150                 155                 160

Leu Leu Gly Val Pro Tyr Ala Asp His Glu Phe Phe Glu Asp Gln Ser
            165                 170                 175

Arg Arg Leu Leu Arg Gly Pro Ala Ala Glu Asp Thr Gln Asp Ala Arg
            180                 185                 190

Asp Arg Leu Ala Ala Tyr Leu Glu Asp Leu Ile Asp Glu Lys Arg Arg
            195                 200                 205

Arg Pro Gly Asp Gly Leu Leu Asp Glu Leu Val Gln Gln Arg Leu Asn
210                 215                 220

Glu Gly Glu Leu Asp Arg Glu Glu Leu Thr Ala Leu Ala Met Ile Leu
225                 230                 235                 240

Leu Val Ala Gly His Glu Thr Thr Ala Asn Met Ile Ser Leu Gly Thr
            245                 250                 255

Tyr Thr Leu Leu Leu His Pro Glu Arg Leu Thr Glu Leu Arg Ala Asp
            260                 265                 270

Pro Ala Leu Leu Pro Ala Ala Val Glu Leu Met Arg Met Leu Ser
            275                 280                 285

Ile Ala Asp Gly Leu Leu Arg Gln Ala Thr Glu Asp Ile Glu Ile Ala
290                 295                 300

Gly Thr Thr Ile Arg Ala Gly Asp Gly Val Val Phe Ser Thr Ser Val
305                 310                 315                 320

Ile Asn Arg Asp Glu Asp Val Tyr Pro Ala Pro Asp Thr Leu Asp Phe
            325                 330                 335

His Arg Ser Thr Arg His His Val Ala Phe Gly Phe Gly Ile His Gln
            340                 345                 350

Cys Leu Gly Gln Asn Leu Ala Arg Thr Glu Leu Glu Ile Ala Leu Arg
            355                 360                 365

Thr Leu Leu Glu Arg Leu Pro Thr Leu Arg Leu Ala Ala Pro Pro Glu
            370                 375                 380

Glu Ile Pro Phe Lys Pro Gly Asp Thr Ile Gln Gly Met Leu Glu Leu
385                 390                 395                 400

Pro Val Ser Trp

<210> SEQ ID NO 9
<211> LENGTH: 65
<212> TYPE: PRT
<213> ORGANISM: Unknown
<220> FEATURE:
<223> OTHER INFORMATION: Derived from an unknown source

<400> SEQUENCE: 9

Met His Ile Glu Ile Asp Lys Asp Arg Cys Ile Gly Ala Gly Gln Cys
1               5                   10                  15

Ala Leu Thr Ala Pro Gly Val Phe Thr Gln Asp Asp Asp Gly Phe Ser
            20                  25                  30

Asp Leu Leu Pro Gly Arg Glu Asp Gly Ala Gly Asp Pro Met Val Arg
            35                  40                  45

Glu Ala Ala Arg Ala Cys Pro Val Ser Ala Ile Thr Leu Ser Glu Asp
        50                  55                  60

Gly
65

<210> SEQ ID NO 10
<211> LENGTH: 29
<212> TYPE: DNA
<213> ORGANISM: Artificial Sequence
```

```
<220> FEATURE:
<223> OTHER INFORMATION: Description of Artificial Sequence : 5Dm-3F
      Primer

<400> SEQUENCE: 10
ttcgcsctsc csgtcccstc satggtsat                                         29

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence : 5Dm-3R
      Primer

<400> SEQUENCE: 11
gttgatsays gasgtsgaga a                                                 21

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence : 6PIN-2F
      Primer

<400> SEQUENCE: 12
gctgcgcctg gccctggagg acatcgagat                                        30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence : 6PIN-2R
      Primer

<400> SEQUENCE: 13
ctgttcctcg aagaactcgt ggtcggcgta                                        30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence : DM-NdeF
      Primer

<400> SEQUENCE: 14
gcccccatat gacggaactg acggacatca                                        30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence : DM-SpeR
      Primer

<400> SEQUENCE: 15
gggccactag tcagccggcc ggttcggtca                                        30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence : DM-BglF
```

```
                                          Primer

<400> SEQUENCE: 16
cgcatagatc ttcacccgag cgggtgatca                                    30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence : DM-BglR
      Primer

<400> SEQUENCE: 17
tcccgagatc ttgaaggtcc gcgtcaccgt                                    30

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence : 5D-1R
      Primer

<400> SEQUENCE: 18
aggtgcccag cgagatcatg tt                                            22

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence : 7PIN-2F
      Primer

<400> SEQUENCE: 19
ccatgatcct gctggtggcc ggccatgaga                                    30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence : 07-NdeF
      Primer

<400> SEQUENCE: 20
gccccatatg accgaagcca tccctactt                                     30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence : 07-SpeR
      Primer

<400> SEQUENCE: 21
gccactagtg ctaatcgtcg gtgaccgcaa                                    30

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence : 5Dm-2R
      Primer
```

```
<400> SEQUENCE: 22
ctggatsgtg tcsccsggyt t                                          21

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence : 5PIN-2F
      Primer

<400> SEQUENCE: 23
cggaatccac cagtgcctcg gccagaacct                                 30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence : tpm-NdeF
      Primer

<400> SEQUENCE: 24
ggccccatat gacagacacg acagacctga                                 30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence : tpm-SpeR
      Primer

<400> SEQUENCE: 25
gcgcgactag tccccctacc cgtcctcgga                                 30
```

DNA PARTICIPATING IN HYDROXYLATION OF MACROLIDE COMPOUND

FIELD OF THE INVENTION

The present invention relates to a DNA participating in hydroxylation of a macrolide compound, a method of isolating it, a protein encoded by the DNA, a plasmid carrying the DNA, a transformant obtained by the transformation of the plasmid and a method of producing a 16-position hydroxy macrolide compound by using the transformant.

PRIOR ART

The 12-membered ring macrolide compound 11107D represented by the formula (II):

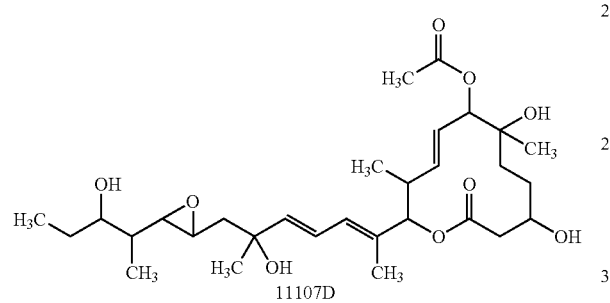

11107D (II)

is a 12-membered ring macrolide compound having an excellent antitumor activity and has been found, together with a 12-membered ring macrolide compound 11107B represented by the formula (I):

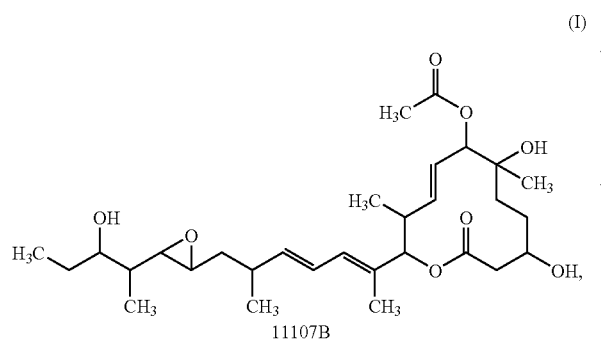

11107B (I)

from a cultured product of a *Streptomyces* sp. Mer-11107 strain (WO02/060890). The macrolide compound 11107D corresponds to a 16-position hydroxylated body of the macrolide compound 11107B. The productivity of the macrolide compound 11107D is lower than that of the macrolide compound 11107B and it has been therefore desired to establish an efficient method of producing the macrolide compound 11107D.

DISCLOSURE OF THE INVENTION

The purpose of the present invention is to find a DNA participating in hydroxylation of the macrolide compound 11107B to thereby provide a novel method of producing the macrolide compound 11107D.

The present invention relates to the following (1) to (15):

(1) a DNA participating in biological transformation of a macrolide compound (hereinafter referred to as a macrolide compound 11107B) represented by the formula (I):

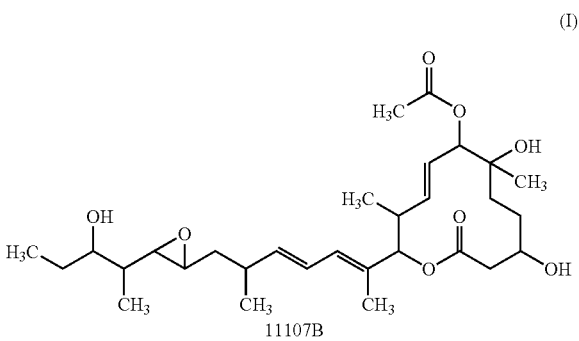

11107B (I)

into a 16-position hydroxy macrolide compound (hereinafter referred to as a macrolide compound 11107D) represented by the formula (II):

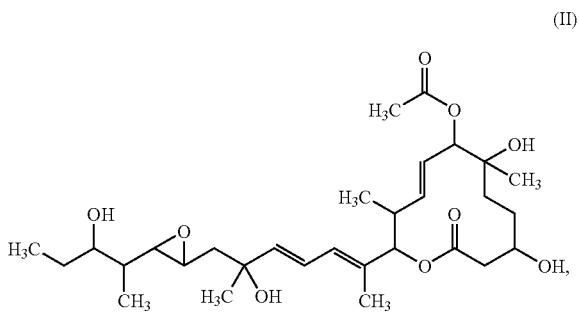

11107D (II)

the DNA being an isolated and pure DNA comprising a DNA encoding a protein having 16-position hydroxylating enzymatic activity or ferredoxin, partly or entirely or its variant;

(2) the DNA described in (1), which is characterized by the following (a), (b) or (c):

a) a DNA encoding a protein having the enzymatic activity in hydroxylating the 16-position of the macrolide compound 11107B and selected from the group consisting of a continuous nucleotide sequence from the base 1322 to base 2548 of SEQ ID NO: 1; a continuous nucleotide sequence from the base 420 to base 1604 of SEQ ID NO: 4; and a continuous nucleotide sequence from the base 172 to base 1383 of SEQ ID NO: 7;

(b) a DNA which is a variant of the DNA described in the above (a);

(i) is hybridized with the DNA described in the above (a) under a stringent condition; and (ii) encodes a protein having enzymatic activity in hydroxylating the 16-position of the macrolide compound 11107B; and (c) a DNA encoding a protein having the same amino acid sequence as the protein encoded by the DNA described in the above (a) or (b) though it is not hybridized with the DNA described in the above (a) under a stringent condition because of the degeneracy of a gene codon;

(3) a protein encoded by the DNA as described in (2);
(4) a self-replicative or integrating replicative recombinant plasmid carrying the DNA as described in (2);
(5) a transformant into which the recombinant plasmid described in (4) transforms;
(6) a method of isolating a DNA encoding a protein having enzymatic activity in hydroxylating the 16-position of the macrolide compound 11107B, the method characterized by using the DNA as described in (2) or a DNA constituted of a part of the DNA as a probe or a primer;
(7) the DNA described in (1), which is characterized by the following (d), (e) or (f):
(e) a DNA which is a variant of the DNA represented by the above (d);
(i) is hybridized with the DNA described in the above (d) under a stringent condition; and
(ii) encodes a protein having a ferredoxin function; and
(f) a DNA encoding a protein having the same amino acid sequence as the protein encoded by the DNA represented by the above (d) or (e) though it is not hybridized with the DNA described in the above (d) under a stringent condition because of the degeneracy of a gene codon;
(8) a protein encoded by the DNA as described in (7);
(9) a self-replicative or integrating replicative recombinant plasmid carrying the DNA as described in (7);
(10) a transformant into which the recombinant plasmid as described in (9) transforms;
(11) a method of isolating a DNA encoding a protein having a ferredoxin function, the method characterized by using the DNA as described in (7) or a DNA constituted of a part of the DNA as a probe or a primer;
(12) a method of producing a 16-position hydroxy macrolide compound, the method comprises the steps of culturing the transformant as described in (5) or (10) in a medium; bringing the proliferated transformant into contact with a macrolide compound represented by the formula (III):

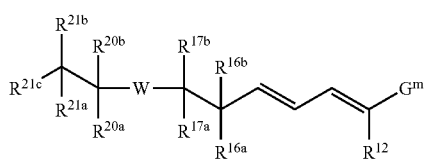

(III)

(wherein W represents

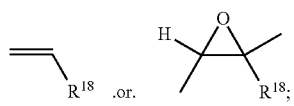

$R^{12}, R^{16b}, R^{17a}, R^{18}, R^{20a}, R^{20b}, R^{21a}$ and $R^{21b}$, which may be the same as or different from, respectively represent:
(1) hydrogen atom;
(2) a $C_{1-22}$ alkyl group which may have a substituent;
(3) —OR (wherein R represents:
  1) hydrogen atom; or
  2) a $C_{1-22}$ alkyl group;
  3) a $C_{7-22}$ aralkyl group;
  4) a 5-membered to 14-membered heteroaryloxyalkyl group;
  5) a $C_{2-22}$ alkanoyl group;
  6) a $C_{7-15}$ aroyl group;
  7) a $C_{3-23}$ unsaturated alkanoyl group;
  8) —$COR^{co}$ (wherein $R^{co}$ represents:
    8-1) a 5-membered to 14-membered heteroaryloxyaryl group;
    8-2) a $C_{1-22}$ alkoxy group;
    8-3) an unsaturated $C_{2-22}$ alkoxy group;
    8-4) a $C_{6-14}$ aryloxy group;
    8-5) a 5-membered to 14-membered heteroaryloxy group; or
    8-6) a 3-membered to 14-membered nitrogen-containing non-aromatic heterocyclic group, each of which may have a substituent);
  9) a $C_{1-22}$ alkylsulfonyl group;
  10) a $C_{6-14}$ arylsulfonyl group; or
  11) —$SiR^{s1}R^{s2}R^{s3}$, (wherein $R^{s1}$, $R^{s2}$ and $R^{s3}$, which may be the same as or different from, respectively represent a $C_{1-6}$ alkyl group or a $C_{6-14}$ aryl group), each of which may have a substituent);
(4) a halogen atom; or
(5) —$R^{M}$—$NR^{N1}R^{N2}$, {wherein $R^{M}$ represents a single bond or —O—CO—; and $R^{N1}$ and $R^{N2}$
1) may be the same as or different from, respectively represent:
  1-1) hydrogen atom; or
  1-2)
    (i) a $C_{1-22}$ alkyl group;
    (ii) an unsaturated $C_{2-22}$ alkyl group;
    (iii) a $C_{2-22}$ alkanoyl group;
    (iv) a $C_{7-15}$ aroyl group;
    (v) an unsaturated $C_{3-23}$ alkanoyl group;
    (vi) a $C_{6-14}$ aryl group;
    (vii) a 5-membered to 14-membered heteroaryl group;
    (viii) a $C_{7-22}$ aralkyl group;
    (ix) a $C_{1-22}$ alkylsulfonyl group; or
    (x) a $C_{6-14}$ arylsulfonyl group, each of which may have a substituent, or
2) and $R^{N1}$ and $R^{N2}$ may be combined with the nitrogen atom to which they bound, to form a 3-membered to 14-membered nitrogen-containing non-aromatic heterocyclic group}, provided that
  $R^{21a}$ and $R^{21b}$ may be combined with each other to form (i) a ketone structure (=O) or (ii) an oxime structure {=$NOR^{ox}$ (wherein $R^{ox}$ represents a $C_{1-22}$ alkyl group, an unsaturated $C_{2-22}$ alkyl group, a $C_{6-14}$ aryl group, a 5-membered to 14-membered heteroaryl group or a $C_{7-22}$ aralkyl group, each of which may have a substituent)};
  $R^{16a}$ represents hydrogen atom;
  $R^{21c}$ represents:
(1) hydrogen atom; or
(2)

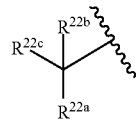

(wherein $R^{22a}$, $R^{22b}$ and $R^{22c}$, which may be the same as or different from, respectively represent:
  1) hydrogen atom;
  2) a $C_{1-6}$ alkyl group;
  3) —OR (wherein R has the same meaning as the above);
  4) —$R^{M}$—$NR^{N1}R^{N2}$ (wherein $R^{M}$, $R^{N1}$ and $R^{N2}$ have the same meanings as the above); or
  5) a halogen atom, or any one of $R^{21a}$ and $R^{21b}$ may be combined with any one of $R^{22a}$ and $R^{22b}$ to form the partial structure;

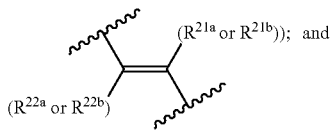

$G^m$ represents:
(1) a group represented by the formula (GM-I):

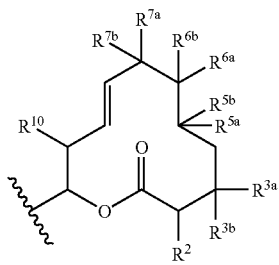

(GM-I)

wherein
$R^2$ and $R^{10}$, which may be the same as or different from, respectively represent hydrogen atom or a $C_{1-22}$ alkyl group;
$R^{3a}, R^{3b}, R^{5a}, R^{5b}, R^{6a}$ and $R^{6b}$, which may be the same as or different from, respectively represent:
1) hydrogen atom;
2) hydroxyl group;
3)
   3-1) a $C_{1-22}$ alkyl group;
   3-2) a $C_{1-22}$ alkoxy group;
   3-3) a $C_{6-14}$ aryloxy group;
   3-4) a 5-membered to 14-membered heteroaryloxy group;
   3-5) a $C_{2-22}$ alkanoyloxy group;
   3-6) a $C_{7-15}$ aroyloxy group;
   3-7) a $C_{3-23}$ unsaturated alkanoyloxy group;
   3-8) —OCOR$^{co}$ (wherein R$^{co}$ has the same meaning as the above);
   3-9) a $C_{1-22}$ alkylsulfonyloxy group;
   3-10) a $C_{6-14}$ arylsulfonyloxy group; or
   3-11) —OSiR$^{s1}$R$^{s2}$R$^{s3}$ (wherein R$^{s1}$, R$^{s2}$ and R$^{s3}$ have the same meanings as the above), each of which may have a substituent;
4) a halogen atom; or
5) —R$^M$—NR$^{N1}$R$^{N2}$ (wherein R$^M$, R$^{N1}$ and R$^{N2}$ have the same meanings as the above); or
   $R^{5a}$ and $R^{5b}$ may be combined with each other to form a ketone structure (=O); or
   $R^{6a}$ and $R^{6b}$ may be combined with each other to form a spirooxysilanyl group or an exomethylene group; or
   $R^{7a}$ and $R^{7b}$, which may be the same as or different from, respectively represent hydrogen atom or —OR$^H$ (wherein R$^H$ represents hydrogen atom, a $C_{1-22}$ alkyl group or a $C_{2-22}$ alkanoyl group)};

(2) a group represented by the formula (GM-II):

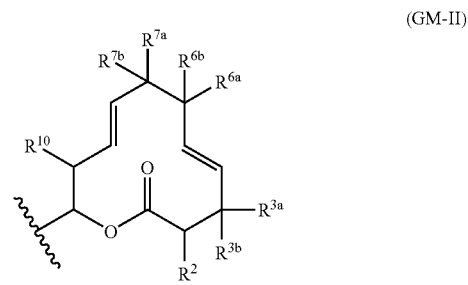

(GM-II)

(wherein $R^2, R^{3a}, R^{3b}, R^{6a}, R^{6b}, R^{7a}, R^{7b}$ and $R^{10}$ have the same meanings as those in the formula (GM-I));
(3) a group represented by the formula (GM-III):

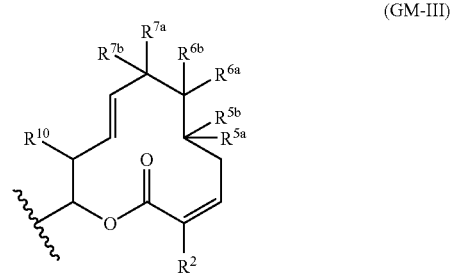

(GM-III)

(wherein $R^2, R^{5a}, R^{5b}, R^{6a}, R^{6b}, R^{7a}, R^{7b}$ and $R^{10}$ have the same meanings as those in the formula (GM-I));
(4) a group represented by the formula (GM-IV):

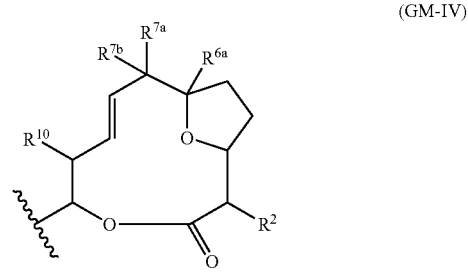

(GM-IV)

(wherein $R^2, R^{6a}, R^{7a}, R^{7b}$ and $R^{10}$ have the same meanings as those in the formula (GM-I)); or
(5) a group represented by the formula (GM-V):

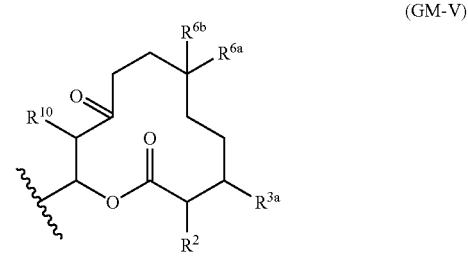

(GM-V)

(wherein $R^2, R^{3a}, R^{6a}, R^{6b}$ and $R^{10}$ have the same meanings as those in the formula (GM-I))) during or after culturing, to convert it into a 16-position hydroxy macrolide compound represented by the formula (IV):

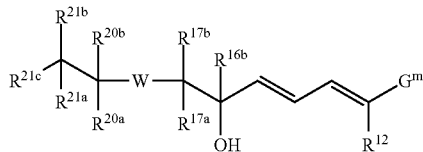

(IV)

(wherein W, $R^{12}$, $R^{16b}$, $R^{17a}$, $R^{17b}$, $R^{20a}$, $R^{20b}$, $R^{21a}$, $R^{21b}$, $R^{21c}$ and $G^m$ have the same meanings as those in the formula (III)); and then collecting the 16-position hydroxy macrolide compound thus converted;

(13) a production method according to (12), wherein the transformant is the transformant as described in (5) and has a DNA encoding ferredoxin;

(14) the production method as described in (12), the method comprises the step of converting a compound represented by the formula (III-a):

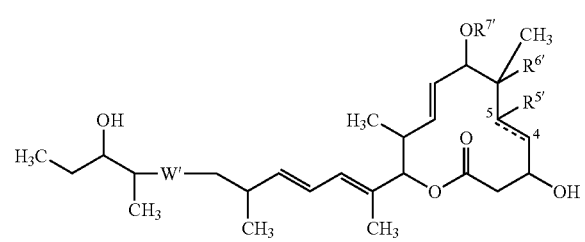

(III-a)

(wherein $^5\text{-----}4$ represents a double bond or a single bond; W' represents a double bond or

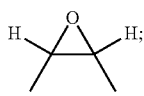

$R^{5'}$ represents hydrogen atom or an acetoxy group; $R^{6'}$ represents hydrogen atom or hydroxyl group; and $R^{7'}$ represents hydrogen atom or acetyl group) into a compound represented by the formula (IV-a):

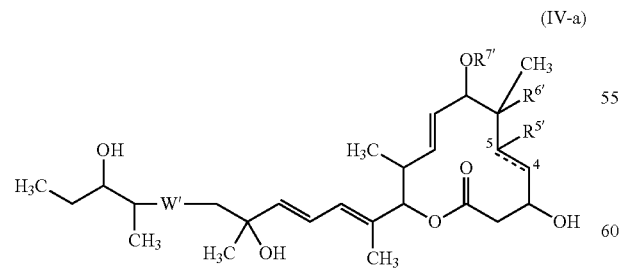

(IV-a)

(wherein $^5\text{-----}4$, W', $R^{5'}$, $R^{6'}$ and $R^{7'}$ have the same meanings as those in the formula (III-a));

(15) the production method as described in (14), wherein, in the conversion of the compound of the formula (III-a) into the compound of the formula (IV-a), the compound to be subjected is a compound selected from the group consisting of:

(1) a compound in which $^5\text{-----}4$ is a single bond; W' is

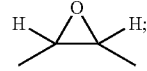

and $R^{5'}$, $R^{6'}$ and $R^{7'}$ are respectively hydrogen atom;

(2) a compound in which $^5\text{-----}4$ is a single bond, W' is

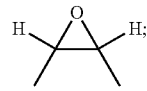

$R^{5'}$ and $R^{6'}$ are respectively hydrogen atom; and $R^{7'}$ is acetyl group;

(3) a compound in which $^5\text{-----}4$ is a single bond, W' is

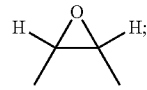

$R^{5'}$ and $R^{7'}$ are respectively hydrogen atom; and $R^{6'}$ is hydroxyl group;

(4) a compound in which $^5\text{-----}4$ is a single bond, W' is

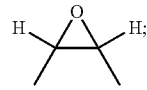

$R^{5'}$ is hydrogen atom, $R^{6'}$ is hydroxy group; and $R^{7'}$ is acetyl group;

(5) a compound in which $^5\text{-----}4$ is a single bond; W' is a double bond; and $R^{5'}$, $R^{6'}$ and $R^{7'}$ are respectively hydrogen atom;

(6) a compound in which $^5\text{-----}4$ is a single bond; W' is a double bond; $R^{5'}$ and $R^{6'}$ are respectively hydrogen atom; and $R^{7'}$ is acetyl group;

(7) a compound in which $^5\text{-----}4$ is a single bond; W' is a double bond; $R^{5'}$ and $R^{7'}$ are respectively hydrogen atom; and $R^{6'}$ is hydroxyl group;

(8) a compound in which $^5\text{-----}4$ is a single bond; W' is a double bond; $R^{5'}$ is hydrogen atom; $R^{6'}$ is hydroxy group; and $R^{7'}$ is acetyl group;

(9) a compound in which $^5\text{-----}4$ is a double bond; W' is

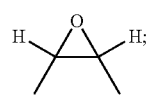

$R^{5'}$ and $R^{7'}$ are respectively hydrogen atom; and $R^{6'}$ is hydroxyl group;

(10) a compound in which $^5\text{-----}4$ is a double bond; W' is $$\text{H} \overset{\text{O}}{\triangle} \text{H};$$

R$^{5'}$ is hydrogen atom; R$^{6'}$ is hydroxy group; and R$^{7'}$ is acetyl group;

(11) a compound in which $^5\text{-----}4$ is a single bond; W' is $$\text{H} \overset{\text{O}}{\triangle} \text{H};$$

R$^{5'}$ is acetoxy group; R$^{6'}$ is hydroxyl group; and R$^{7'}$ is hydrogen atom; and

(12) a compound in which $^5\text{-----}4$ is a single bond; W' is $$\text{H} \overset{\text{O}}{\triangle} \text{H};$$

R$^{5'}$ is an acetoxy group; R$^{6'}$ is hydroxyl group; and R$^{7'}$ is acetyl group; and

(16) use of the transformant as described in (5) or (10) for producing a 16-position hydroxy macrolide compound.

The present invention made it possible to isolate a DNA encoding a protein having the enzymatic activity in hydroxylating the 16-position of a macrolide compound 11107B or ferredoxin and to determine its nucleotide sequence. Moreover, a plasmid carrying the DNA and a transformant into which the plasmid transformed were formed and a 16-position hydroxy macrolide compound could be produced using the transformant in an efficient manner.

Hereinafter, embodiments of the present invention will be explained in detail. Microorganisms having the ability of converting a macrolide compound 11107B into a macrolide compound 11107D In the present invention, a DNA encoding a protein having enzymatic activity in hydroxylating the 16-position or ferredoxin, partly or entirely can be isolated from the mycelia isolated from a culture broth in which microorganisms having the ability of converting the macrolide compound 11107B into the macrolide compound 11107D are cultured and the nucleotide sequence of the DNA can be determined. Then, a self-replicative or integrating replicative recombinant plasmid carrying the DNA is architecturally formed and a transformant is prepared using the plasmid.

The transformant thus prepared is cultured in the culture media and the proliferated transformant is brought into contact with the macrolide compound represented by the above formula (III) during or after culturing, to thereby covert the macrolide compound into the 16-position hydroxy macrolide compound represented by the formula (IV) and the converted 16-position hydroxy macrolide compound is collected, whereby the 16-position hydroxy macrolide compound can be obtained.

Any microorganisms having the ability of converting the macrolide compound 11107B into the macrolide compound 11107D may be used irrespective of the type of species and strain. Preferable examples of the microorganisms may include a *Streptomyces* sp. Mer-11107 or A-1544 strain and an unidentified *Actinomyces* A-1560 strain which were each isolated from soils.

It is to be noted that the *Streptmyces* sp. Mer-11107 was deposited as FERM P-18144 at the National Institute of Bioscience and Human-Technology Agency of Industrial Science and Technology (1-3, Higashi 1-chome Tsukuba-shi, Ibaraki-ken 305-8566 Japan) as of Dec. 19, 2000, and then transferred to International Deposit FERM BP-7812 at International Patent Organism Depositary (IPOD) National Institute of Advanced Industrial Science and Technology (Tsukuba Central 6, 1-1, Higashi 1-Chome, Tsukuba-shi, Ibaraki-ken 305-8566 Japan) as of Nov. 27, 2001. The A-1544 strain was deposited as FERM BP-8446 at International Patent Organism Depositary National Institute of Advanced Industrial Science and Technology (Tsukuba Central 6, 1-1, Higashi 1-Chome, Tsukuba-shi, Ibaraki-ken 305-8566 Japan) as of Jul. 23, 2002, and then transferred to International Deposit FERM BP-8446 as of Jul. 30, 2003, at International Patent Organism Depositary (IPOD) National Institute of Advanced Industrial Science and Technology (Tsukuba Central 6, 1-1, Higashi 1-Chome, Tsukuba-shi, Ibaraki-ken 305-8566 Japan). The A-1560 strain was deposited as FERM P-19585 at International Patent Organism Depositary National Institute of Advanced Industrial Science and Technology (Tsukuba Central 6, 1-1, Higashi 1-Chome, Tsukuba-shi, Ibaraki-ken 305-8566 Japan) as of Nov. 13, 2003 and then transferred to International Deposit FERM BP-10102 as of Aug. 19, 2004, at International Patent Organism Depositary (IPOD) National Institute of Advanced Industrial Science and Technology (Tsukuba Central 6, 1-1, Higashi 1-Chome, Tsukuba-shi, Ibaraki-ken 305-8566 Japan).

The taxonomical properties of the above strains are as follows.

(Taxonomical Properties of the Mer-11107 Strain)

(1) Morphological Characteristics

Spiriles type aerial hyphae were extended from the vegetative hyphae. Spore chains consisting of about 10 to 20 cylindrical spores were formed at the end of the matured aerial hyphae. The size of the spores was about 0.7×1.0 μm, the surface of the spores was smooth, and specific organs such as sporangium, sclerotium and flagellum were not observed.

(2) Cultural Characteristics on Various Media

Cultural characteristics of the strain after incubation at 28° C. for two weeks on various media are shown as follows. The color tone is described by the color names and codes which are shown in the parentheses of Tresner's Color wheels.

1) Yeast Extract-Malt Extract Agar Medium

The strain grew well, the aerial hyphae grew upon the surface, and light gray spores (Light gray; d) were observed. The reverse side of colony was Light melon yellow (3ea). Soluble pigment was not produced.

2) Oatmeal Agar Medium

The strain grew moderately, the aerial hyphae grew slightly on the surface, and gray spores (Gray; g) were observed. The reverse side of colony was Nude tan (4gc) or Putty (1½ec). Soluble pigment was not produced.

3) Inorganic Salts-Starch Agar Medium

The strain grew well, the aerial hyphae grew upon the surface, and gray spores (Gray; e) were observed. The reverse side of colony was Fawn (4ig) or Gray (g). Soluble pigment was not produced.

4) Glycerol-Asparagine Agar Medium

The strain grew well, the aerial hyphae grew upon the surface, and white spores (White; a) were observed. The reverse side of colony was Pearl pink (3ca). Soluble pigment was not produced.

5) Peptone-Yeast Extract-Iron Agar Medium

The strain growth was bad, and the aerial hyphae did not grow on the surface. The reverse side of colony was Light melon yellow (3ea). Soluble pigment was not produced.

6) Tyrosine Agar Medium

The strain grew well, the aerial hyphae grew upon the surface, and white spores (White; a) were observed. The reverse side of colony was Pearl pink (3ca). Soluble pigment was not produced.

(3) Utilization of Various Carbon Sources

Various carbon sources were added to Pridham-Gottlieb agar and incubated 28° C. for 2 weeks. The growth of the strain is shown below.

1) L-arabinose ±
2) D-xylose ±
3) D-glucose +
4) D-fructose +
5) Sucrose +
6) Inositol +
7) L-rhamnose −
8) D-mannitol +
9) Raffinose +
(+ positive, ± slightly positive, − negative)

(4) Various Physiological Properties

Various physiological properties of the present strain are as follows.

(a) Range of growth temperature (yeast extract-malt extract agar, incubation for 2 weeks): 12° C. to 37° C.
(b) Range of optimum growth temperature (yeast extract-malt extract agar, incubation for 2 weeks): 21° C. to 33° C.
(c) Liquefaction of gelatin (glucose-peptone-gelatin medium) negative
(d) Coagulation of milk (skim milk medium): negative
(e) Peptonization of milk (skim milk medium): negative
(f) Hydrolysis of starch (inorganic salts-starch agar): positive
(g) Formation of melanoid pigment (peptone-yeast extract-iron agar): negative
(tyrosine agar): negative
(h) Production of hydrogen sulfide (peptone-yeast extract-iron agar): negative
(i) Reduction of nitrate (broth containing 0.1% potassium nitrate): negative
(j) Sodium chloride tolerance (yeast extract-malt extract agar, incubation for 2 weeks): grown at a salt content of 4% or less (5) Chemotaxonomy LL-diaminopimelic acid and glycin were detected from the cell wall of the present strain.

(Taxonomical Properties of the A-1544 Strain)

(1) Morphological Characteristics

Spira type aerial hyphae were extended from vegetative hyphae in this strain. Spore chains consisting of about 10 to 20 of cylindrical spores were formed at the end of the matured aerial hyphae. The size of the spores was about 1.0×1.2 to 1.4 μm, the surface of the spores was spiny, and specific organs such as sporangium, sclerotium and flagellum were not observed.

(2) Cultural Characteristics on Various Media

Cultural characteristics of the strain after incubation at 28° C. for two weeks on various media are shown in Table 1. The color tone is described by the color names and codes which are shown in the parentheses of Tresner's Color wheels.

TABLE 1

| Medium | Growth | Aerial hyphae | Color of vegetative hyphae | Soluble pigment |
|---|---|---|---|---|
| Yeast extract - malt extract agar (ISP-2) | Good | Thick Silver gray (3fe) | Light melon yellow (3ea) | None |
| Oatmeal agar (ISP-3) | Good | Abundant Light gray to Silver gray (d to 3fe) | Light melon yellow (3ea) | None |
| Inorganic salts - starch agar (ISP-4) | Good | Abundant Silver gray (3fe) | Light melon yellow (3ea) | None |
| Glycerol - asparagine agar (ISP-5) | Good | Abundant Ashes (5fe) | Light melon yellow (3ea) | None |
| Peptone-yeast extract - iron agar (ISP-6) | Good | None | Light melon yellow (3ea) | Pale blackish brown |
| Tyrosine agar (ISP-7) | Good | Abundant Covert gray (2fe) | Light melon yellow (3ea) | None |

(3) Utilization of Various Carbon Sources

Various carbon sources were added to Pridham-Gottlieb agar and incubated at 28° C. for 2 weeks. The growth of the strain is shown in Table 2.

TABLE 2

| D-glucose | + | inositol | − |
|---|---|---|---|
| L-arabinose | + | L-rhamnose | + |
| D-xylose | + | D-mannitol | + |
| D-fructose | + | raffinose | − |
| sucrose | − | | |

+: positive,
±: slightly positive,
−: negative (4) Various Physiological Properties Various physiological properties of the present strain are as follows.

(a) Range of growth temperature (yeast extract-malt extract agar, incubation for 2 weeks): 15° C. to 41° C.
(b) Range of optimum growth temperature (yeast extract-malt extract agar, incubation for 2 weeks): 2°° C. to 37° C.
(c) Liquefaction of gelatin (glucose-peptone-gelatin medium) positive
(d) Coagulation of milk (skim milk medium): positive
(e) Peptonization of milk (skim milk medium): positive
(f) Hydrolysis of starch (inorganic salts-starch agar): positive
(g) Formation of melanoid pigment (peptone-yeast extract-iron agar): positive (tyrosine agar): negative
(h) Production of hydrogen sulfide (peptone-yeast extract-iron agar): positive
(i) Reduction of nitrate (broth containing 0.1% potassium nitrate): negative
(j) Sodium chloride tolerance (yeast extract-malt extract agar, incubation for 2 weeks): grown at a salt content of 7% or less (5) Chemotaxonomy LL-diaminopimelic acid was detected from the cell wall of the present strain.

DNA of the Present Invention

The present inventors have isolated a DNA participating in the hydroxylation of the 16-position of a macrolide compound, specifically, a DNA encoding a protein having 16-position hydroxylating enzymatic activity and a DNA encoding a protein having a ferredoxin function from the above microorganisms and determined the nucleotide sequence of the DNA. The DNA encoding a protein having 16-position hydroxylating enzymatic activity and the DNA encoding a protein having a ferredoxin function are hereinafter generically called "a 16-position hydroxylating enzyme relevant DNA" as the case may be.

The DNA encoding a protein having 16-position hydroxylating enzymatic activity is those represented by the following (1-1), (1-2) or (1-3):
(1-1) a DNA selected from those having a continuous nucleotide sequence from the base 1322 to base 2548 of SEQ ID NO: 1, a continuous nucleotide sequence from the base 420 to base 1604 of SEQ ID NO: 4 and a continuous nucleotide sequence from the base 172 to base 1383 of SEQ ID NO: 7;
(1-2) a DNA which is a variant of the DNA described in the above (1-1);
(i) is hybridized with any one of the DNAs described in the above (1-1) under a stringent condition; and
(ii) codes a protein having enzymatic activity in hydroxylating the 16-position of the macrolide compound; and
(1-3) a DNA encoding a protein having the same amino acid sequence as the protein encoded by the DNA described in the above (1-1) or (1-2) though it is not hybridized with any of the DNA described in the above (1-1) or (1-2) under a stringent condition because of the degeneracy of a gene codon.

The "16-position hydroxylating enzymatic activity" means such enzymatic activity as to hydroxylate the 16-position of the macrolide compound 11107B represented by the formula (I) to thereby convert the macrolide compound into the macrolide compound 11107D represented by the formula (II).

The DNA encoding a protein having a ferredoxin function in the present invention is those represented by the following (2-1), (2-2) or (2-3).
(2-1) a DNA encoding ferredoxin and selected from the group consisting of a continuous nucleotide sequence from the base 2564 to base 2761 of SEQ ID NO: 1, a continuous nucleotide sequence from the base 1643 to base 1834 of SEQ ID NO: 4 and a continuous nucleotide sequence from the base 1399 to base 1593 of SEQ ID NO: 7;
(2-2) a DNA which is a variant of the DNA described in the above (2-1);
(i) is hybridized with the DNA described in the above (2-1) under a stringent condition; and
(ii) codes a protein having a ferredoxin function; and
(2-3) a DNA encoding a protein having the same amino acid sequence as the protein encoded by the DNA represented by the above (2-1) or (2-2) though it is not hybridized with the DNA represented by the above (2-1) under a stringent condition because of the degeneracy of a gene codon.

"The ferredoxin function" means the protein function of transferring electrons to the above 16-position hydroxylating enzyme to bear a role together with the above 16-position hydroxylating enzyme in the hydroxylation reaction.

Also, "the nucleotide sequence hybridized under a stringent condition" means a DNA nucleotide sequence obtained when any one of the DNAs of the above (1-1) and (1-2) is used as a probe and, for example, a colony hybridization method, plaque hybridization method or Southern blot hybridization method is used. Examples of the DNA having such a nucleotide sequence may include those identified by carrying out hybridization in the presence of 0.7 to 1.0 M NaCl at 65° C. using a filter to which a DNA derived from a colony or a plaque or a fragment of the DNA is fixed and then washing the filter at 65° C. by using 0.1 to 2×SSC solution (1×SSC solution: 150 mM sodium chloride and 15 mM sodium citrate). The hybridization may be carried out according to the method described in Molecular Cloning: A laboratory Manual, 2nd Ed., Cold Spring Harbor Laboratory, Cold Spring Harbor, N.Y., 1989 (hereinafter abbreviated as molecular cloning, 2nd ed.).

Examples of the DNA hybridized in a stringent condition include DNAs having a nucleotide sequence having a certain level or more of homology with the nucleotide sequence of the DNA to be used as the probe, and specifically DNAs having a nucleotide sequence having 80% or more, preferably 85% or more, more preferably 90% or more, still more preferably 95% or more and most preferably 98% or more homology with the nucleotide sequence of the DNA used as the probe.

There is no particular limitation to a method of obtaining the 16-position hydroxylating enzyme relevant DNA. An appropriate probe or a primer is prepared based on the information of the nucleotide sequence described in the sequence No. 1, No. 2 or No. 3 of the sequence chart in this specification. Using the probe or primer, a DNA library of microorganisms belonging to Actinomyces is screened, and thus the DNA of the present invention can be isolated. The DNA library can be produced by the usual method from microorganisms expressing the aforementioned 16-position hydroxylating enzymatic activity.

The 16-position hydroxylating enzyme relevant DNA of the present invention can also be obtained by a PCR method. A DNA library derived from the aforementioned microorganisms is used as a template and a pair of primers which are so designed as to amplify any one of the nucleotide sequences described in the sequence No. 1, No. 2 or No. 3 are used to carry out PCR. The reaction condition of the PCR may be appropriately designed. Examples of the reaction condition may include the condition of a process in which the cycle of the process involving a reaction run at 94° C. for 30 seconds (denaturing), a reaction run at 55° C. for 30 seconds to one minute (annealing) and a reaction run at 72° C. for 2 minutes (extension) is repeated 30 times and then a reaction is run at 72° C. for 7 minutes. Then, the amplified DNA fragment can be cloned in a vector which can be amplified in a proper host.

The aforementioned operations such as the preparation of a probe or a primer, the construction of a DNA library, the screening of a DNA library and the cloning of a target gene are obvious to a person skilled in the art and may be carried out according to methods as described in for example, Molecular Cloning 2nd ed., Current Protocols in Molecular Biology, Supplement 1 to 38, John Wiley & Sons (1987-1997).

No particular limitation is imposed on a method of obtaining the protein in the present invention. The protein may be a protein synthesized by chemical synthesis or a recombinant protein produced by gene recombination techniques. When the recombinant protein is produced, first, the DNA encoding the protein as described above in this specification is obtained. The protein of the present invention can be produced by introducing this DNA into a proper expression system. Manifestation of the protein in the expression system will be described later in the specification.

Recombinant Vector in the Present Invention

The DNA of the present invention may be used in the situation where it is inserted in an appropriate vector. No particular limitation is imposed on the kind of the vector to be used in the present invention and the vector may be either a self-replicative one (for example, a plasmid) or one that is incorporated into a genome of a host cell when introduced into the host cell and is replicated together with the incorporated chromosome. In the expression vector, the DNA of the present invention is operationally linked to elements (for example, a promoter) which are necessary for transcription. The promoter is a DNA sequence exhibiting transcriptional activity in a host cell and may be selected suitably corresponding to the type of host.

The Transformant of the Present Invention and Production of a Recombinant Protein Using the Transformant The transformant may be produced by introducing the DNA or recombinant vector of the present invention into an appropriate host. The host cell into which the DNA or recombinant vector of the present invention is introduced may be any desired cell which can express the gene according to the present invention. Examples of the host cell include bacteria, yeast, fungi and higher eucaryotec cells. Examples of the bacterial cell include Gram-positive bacteria such as *Bacillus* or *Streptomyces* or Gram-negative bacteria such as *E. coli*. The transformation of these bacteria may be accomplished using a competent cell according to a protoplast method, electro-poration method or other known methods. For example, the electroporation method may be performed as follows. A plasmid into which a foreign gene is inserted is added to a suspension of the competent cell, this suspension is poured into a cuvet specially used for an electroporation method and high-voltage electric pulse is applied to the cuvet. Then, the cells are cultured in a selective medium and a transformant is isolated on a plate agar media.

Examples of the yeast cell include cells belonging to *Saccharomyces* or *Schizosaccharomyces*. Specific examples of the yeast cell include *Saccharomyces cerevisiae* or *Saccharomyces kluyveri*. Examples of a method of introducing the recombinant vector into the yeast host may include an electroporation method, spheroplasto method and lithium acetate method. Examples of the above other fungus cell include mycotic cells belonging to *Aspergillus, Neurospora, Fusarium* or *Trichoderma*. When mold fungi are used as the host cell, a DNA architecture is incorporated into a host chromosome to obtain a recombinant host cell, whereby transformation can be accomplished. The incorporation of the DNA architecture into the host chromosome can be accomplished, for example, by homologous recombination or heterologous recombination.

The above transformant is cultured in an appropriate nutrient medium under the condition enabling the expression of the introduced gene. In order to isolate the protein of the invention from the culture product of the transformant and to purify the protein, the usual protein isolating and purifying method may be used.

For example, when the protein of the present invention is expressed in a soluble form in cells, the cells are collected by centrifugation after the cultivation is finished and are suspended in a buffer solution. Then, the suspended solution is subjected to, for example, a ultrasonic crusher to break the cells, thereby obtaining a cell-free extract and the cell-free extract is centrifuged. A purified preparation can be obtained from the obtained supernatant by combining measures such as the usual isolation and purifying methods such as a solvent extraction method, salting-out method using ammonium sulfate, desalting method, precipitation method using an organic solvent, anion exchange chromatography using a resin such as diethylaminoethyl (DEAE) sepharose, cation exchange chromatography using a resin such as SP-Sepharose FF (manufactured by Amasham Bioscience Company), hydrophobic chromatography using a resin such as butyl sepharose and phenyl sepharose, gel filtration method using a molecular sieve, affinity chromatography, chromato-focusing method and electrophoresis method such as an isoelectric focusing electrophoresis.

Method of Production of 16-Position Hydroxy Macrolide Compounds

The present invention involves a method of producing 16-position hydroxy macrolide compounds represented by the above formula (IV), the method comprising using a transformant into which a DNA encoding a protein having 16-position hydroxylating enzymatic activity or a protein having a ferredoxin function is introduced and hydroxylating macrolide compounds represented by the above formula (III) in the presence of the transformant.

The macrolide compounds that can be hydroxylated by the transformant of the present invention is macrolide compounds represented by the above formula (III) (macrolide compounds represented by the above formula (IV)), preferably macrolide compounds represented by the above formula (III-a) (macrolide compounds represented by the above formula (IV-a) and more preferably the macrolide compound 11107B (macrolide compound 11107D). The compounds in the parenthesis are 16-position hydroxy macrolide compounds that are hydroxylated products.

The condition under which the macrolide compounds are hydroxylated in the presence of the transformant is as follows.

First, the 16-position hydroxylating enzyme relevant DNA in the transformant is expressed by adding, if necessary, inducing materials. The strain expressing the DNA is brought into contact with the macrolide compounds represented by the above formula (III) to run a conversion reaction. The temperature of the conversion reaction may be suitably determined taking the optimum growth temperature of the transformant into account. The reaction time may also be suitably determined in consideration of the conversion rate (degree of progress of the reaction) into the 16-position hydroxy macrolide compound. For example, the condition of 20 to 31° C. and 1 to 5 days is preferable. Moreover, as to the reaction system, the reaction may be run in any system including a batch system or a continuous system.

For the isolation and purifying of the produced 16-position hydroxy macrolide compounds, the separation and purifying method used usually to isolate a microbial metabolite from the culture broth may be utilized. All known separation and purifying methods such as organic solvent extraction using methanol, ethanol, acetone, butanol, ethyl acetate, butyl acetate, chloroform or toluene, absorption chromatograph using a hydrophobic adhesive resin such as Diaion HP-20, gel filtration chromatography using Sefadex LH-20, adsorption chromatography using activated carbon, silica gel or the like, absorption chromatograph using thin-layer chromatography and high-performance liquid chromatography using an reverse phase column are equivalent to these separation and purifying methods. The separation and purifying method is not limited to these methods shown here. These methods may be used singly or in combinations of two or more in an optional order or repeatedly, which makes it possible to isolate and purify the target 16-position hydroxy macrolide compounds.

The variant of the DNA in the present invention means a DNA that is obtained by modifying the DNA by deletion, conversion, addition or insertion treatments in the structural base of the DNA or its derivatives and shows the same effects as the original DNA.

The "halogen atom" used in the specification of the present application means a fluorine atom, a chlorine atom, a bromine atom and an iodine atom.

The "$C_{1-22}$ alkyl group" used in the specification of the present application indicates a linear or branched alkyl group having 1 to 22 carbon atoms, such as methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 1-ethylbutyl group, 2-ethylbutyl group, 2-methylpentyl group, 3-methylpentyl group, n-heptyl group, n-octyl group, n-nonyl group or n-decyl group; preferably a linear or branched alkyl group having 1 to 6 carbon atoms, such as methyl group, ethyl group, n-propyl group, iso-propyl group, n-butyl group, iso-butyl group, sec-butyl group or tert-butyl group.

The "unsaturated $C_{2-22}$ alkyl group" used in the specification of the present application indicates a linear or branched alkenyl group having 2 to 22 carbon atoms or a linear or branched alkynyl group having 2 to 22 carbon atoms, such as vinyl group, allyl group, 1-propenyl group, isopropenyl group, 2-methyl-1-propenyl group, 2-methyl-2-propenyl group, 1-butenyl group, 2-butenyl group, 3-butenyl group, 1-pentenyl group, 1-hexenyl group, 1,3-hexadienyl group, 1,5-hexadienyl group, ethynyl group, 1-propynyl group, 2-propynyl group, 1-butynyl group, 2-butynyl group, 3-butynyl group, 1-ethynyl-2-propynyl group, 2-methyl-2-propynyl group, 1-pentynyl group, 1-hexynyl group, 1,3-hexadiynyl group or 1,5-hexadiynyl group. It preferably indicates a linear or branched alkenyl group having 2 to 10 carbon atoms or a linear or branched alkynyl group having 2 to 10 carbon atoms, such as vinyl group, allyl group, 1-propenyl group, isopropenyl group, ethynyl group, 1-propynyl group, 2-propynyl group, 1-butynyl group, 2-butynyl group or 3-butynyl group.

The "$C_{6-14}$ aryl group" used in the specification of the present application means an aromatic hydrocarbon group having 6 to 14 carbon atoms, and a monocyclic group and condensed rings such as a bicyclic group and a tricyclic group are included. Examples thereof are phenyl group, indenyl group, 1-naphthyl group, 2-naphthyl group, azulenyl group, heptalenyl group, indacenyl group, acenaphthyl group, fluorenyl group, phenalenyl group, phenanthrenyl group and anthracenyl group; of which a preferred example is phenyl group, 1-naphthyl group or 2-naphthyl group.

The "5-membered to 14-membered heteroaryl group" used in the specification of the present application means a monocyclic, bicyclic or tricyclic 5-membered to 14-membered aromatic heterocyclic group which contains one or more of hetero atoms selected from the group consisting of a nitrogen atom, sulfur atom and oxygen atom. Preferred examples thereof are a nitrogen-containing aromatic heterocyclic group such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazinyl group, naphthyridinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridinyl group, imidazopyrimidinyl group, or pyrazolopyridyl group; a sulfur-containing aromatic heterocyclic group such as thienyl group or benzothienyl group; and an oxygen-containing aromatic heterocyclic group such as furyl group, pyranyl group, cyclopentapyranyl group, benzofuranyl group or isobenzofuranyl group; an aromatic heterocyclic group containing two or more different hetero atoms, such as thiazolyl group, isothiazolyl group, benzothiazolyl group, benzothiadiazolyl group, phenothiazinyl group, isoxazolyl group, furazanyl group, phenoxazinyl group, oxazolyl group, isoxazoyl group, benzoxazolyl group, oxadiazolyl group, pyrazolooxazolyl group, imidazothiazolyl group, thienofuranyl group, furopyrrolyl group or pyridoxazinyl group, of which a preferred example is thienyl group, furyl group, pyridyl group, pyridazinyl group, pyrimidinyl group or pyrazinyl group.

The "3-membered to 14-membered nitrogen-containing non-aromatic heterocyclic group" used in the specification of the present application means a monocyclic, bicyclic or tricyclic 3-membered to 14-membered non-aromatic heterocyclic group containing one or more nitrogen atoms. Preferable examples thereof include an azilidinyl group, azetizyl group, pyrrolidinyl group, pyrrolyl group, piperidyl group, piperazinyl group, homopiperidinyl group, homopiperazinyl group, imidazolyl group, pyrazolidinyl group, imidazolidinyl, morpholinyl group, thiomorpholinyl group, imidazolinyl group, oxazolinyl group and quinuclidinyl group. The nitrogen-containing non-aromatic heterocyclic group also includes a group derived from a pyridone ring and a non-aromatic condensed ring (such as a group derived from a phthalimide ring or succinimide ring).

The "$C_{2-22}$ alkanoyl group" used in the specification of the present application means a group corresponding to the above-defined "$C_{1-22}$ alkyl group" in which the end thereof is a carbonyl group. Examples thereof include acetyl group, propionyl group, butyryl group, iso-butyryl group, valeryl group, iso-valeryl group, pivaloyl pivalyl group, caproyl group, decanoyl group, lauroyl group, myristoyl group, palmitoyl group, stearoyl group and arachidoyl group. Preferable examples thereof include alkanoyl groups having 2 to 6 carbon atoms such as acetyl group, propionyl group, butyryl group or iso-butyryl group.

The "$C_{7-15}$ aroyl group" used in the specification of the present application means a group corresponding to the above-defined "$C_{6-14}$ aryl group" or "5-membered to 14-membered heteroaryl group" to each of which end a carbonyl group is bonded. Examples thereof include benzoyl group, 1-naphthoyl group, 2-naphthoyl group, picolinoyl group, nicotinoyl group, isonicotinoyl group and furoyl group.

The "$C_{3-23}$ unsaturated alkanoyl group" used in the specification of the present application means a group corresponding to the above-defined "unsaturated $C_{2-22}$ alkyl group" to which end a carbonyl group is bonded. Examples thereof include an acryloyl group, propioloyl group, crotonoyl group, iso-crotonoyl group, oleoyl group and linolenoyl group. Preferable examples thereof include unsaturated alkanoyl groups having 2 to 6 carbon atoms and specifically an acryloyl group.

The "$C_{7-22}$ aralkyl group" used in the specification of the present application means a group corresponding to the above-defined "$C_{1-22}$ alkyl group" of which substitutable moiety is replaced by the above-defined "$C_{6-14}$ aryl group" and being constituted of 7 to 22 carbon atoms. Specific examples thereof are benzyl group, phenethyl group, 3-phenylpropyl group, 4-phenylbutyl group, 1-naphthylmethyl group and 2-naphthylmethyl group, of which an aralkyl group having 7 to 10 carbon atoms such as benzyl group or phenethyl group is preferred.

The "$C_{1-22}$ alkoxy group" used in the specification of the present application means a group corresponding to the above-defined "$C_{1-22}$ alkyl group" to which end an oxygen atom is bonded. Suitable examples thereof are methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-dimethylpropoxy group, 2,2-dimethylpropoxy group, 2-ethylpropoxy group, 1-ethyl-2-methylpropoxy group, 1,1,2-trimethylpropoxy group, 1,2,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 1,3-dimethylbutoxy group, 2-methylpentyloxy group and 3-methylpentyloxy group.

The "unsaturated $C_{2-22}$ alkoxy group" used in the specification of the present application means a group corresponding to the above-defined "unsaturated $C_{2-22}$ alkyl group" to which end an oxygen atom is bonded. Suitable examples thereof are vinyloxy group, allyloxy group, 1-propenyloxy group, isopropenyloxy group, 2-methyl-1-propenyloxy group, 2-methyl-2-propenyloxy group, 1-butenyloxy group, 2-butenyloxy group, 3-butenyloxy group, 1-pentenyloxy group, 1-hexenyloxy group, 1,3-hexadienyloxy group, 1,5-hexadienyloxy group, propargyloxy group and 2-butynyloxy group.

The "$C_{6-14}$ aryloxy group" used in the specification of the present application means a group corresponding to the above-defined "$C_{6-14}$ aryl group" to which end an oxygen atom is bonded. Specific examples thereof are phenoxy group, indenyloxy group, 1-naphthyloxy group, 2-naphthyloxy group, azulenyloxy group, heptalenyloxy group, indacenyloxy group, acenaphthyloxy group, fluorenyloxy group, phenalenyloxy group, phenanthrenyloxy group and anthracenyloxy group.

The "5-membered to 14-membered heteroaryloxy group" used in the specification of the present application means a group corresponding to the above-defined "5-membered to 14-membered heteroaryl group" to which end an oxygen atom is bonded. Specific examples thereof are pyrrolyloxy group, pyridyloxy group, pyridazinyloxy group, pyrimidinyloxy group, pyrazinyloxy group, triazolyloxy group, tetrazolyloxy group, benzotriazolyloxy group, pyrazolyloxy group, imidazolyloxy group, benzimidazolyloxy group, indolyloxy group, isoindolyloxy group, indolizinyloxy group, purinyloxy group, indazolyloxy group, quinolyloxy group, isoquinolyloxy group, quinolizinyloxy group, phthalazinyloxy group, naphthyridinyloxy group, quinoxalinyloxy group, quinazolinyloxy group, cinnolinyloxy group, pteridinyloxy group, imidazotriazinyloxy group, pyrazinopyridazinyloxy group, acridinyloxy group, phenanthridinyloxy group, carbazolyloxy group, carbazolinyloxy group, perimidinyloxy group, phenanthrolinyloxy group, phenazinyloxy group, imidazopyridinyloxy group, imidazopyrimidinyloxy group, pyrazolopyridyloxy group, thienyloxy group, benzothienyloxy group, furyloxy group, pyranyloxy group, cyclopentapyranyloxy group, benzofuryloxy group, isobenzofuryloxy group, thiazolyloxy group, isothiazolyloxy group, benzothiazolyloxy group, benzothiadiazolyloxy group, phenothiazinyloxy group, isoxazolyloxy group, furazanyloxy group, phenoxazinyloxy group, oxazolyloxy group, isoxazoyloxy group, benzoxazolyloxy group, oxadiazolyloxy group, pyrazolooxazolyloxy group, imidazothiazolyloxy group, thienofuranyloxy group, furopyrrolyloxy group and pyridoxazinyloxy group, of which a preferred example is thienyloxy group, furyloxy group, pyridyloxy group, pyridazyloxy group, pyrimidyloxy group or pyrazyloxy group.

The "5-membered to 14-membered heteroaryloxyalkyl group" used in the specification of the present application means a group corresponding to the above-defined "$C_{1-6}$ alkyl group" which is substituted with the above-defined "5-membered to 14-membered heteroaryloxy group".

The "$C_{1-22}$ alkylsulfonyl group" used in the specification of the present application means a sulfonyl group to which the above-defined "$C_{1-22}$ alkyl group" is bound. Specific examples thereof are methanesulfonyl group, ethanesulfonyl group, n-propanesulfonyl group and iso-propanesulfonyl group.

The "$C_{6-14}$ arylsulfonyl group" used in the specification of the present application means a sulfonyl group to which the above-defined "$C_{6-14}$ aryl group" is bound. Specific examples thereof are benzenesulfonyl group, 1-naphthalenesulfonyl group and 2-naphthalenesulfonyl group.

The "$C_{1-22}$ alkylsulfonyloxy group" used in the specification of the present application means a group corresponding to the above-defined "$C_{1-22}$ alkylsulfonyl group" to which end an oxygen atom is bonded. Examples thereof are methylsulfonyloxy group, ethylsulfonyloxy group, n-propylsulfonyloxy group and iso-propylsulfonyloxy group.

Examples of the substituent in the term "may have a substituent" used in the specification of the present application include those selected from the group consisting of:

(1) halogen atom;
(2) hydroxyl group;
(3) thiol group;
(4) nitro group;
(5) nitroso group;
(6) cyano group;
(7) carboxyl group;
(8) sulfonyloxy group;
(9) amino group;
(10) a $C_{1-22}$ alkyl group (for example, methyl group, ethyl group, n-propyl group, iso-propyl group, n-butyl group, iso-butyl group, sec-butyl group and tert-butyl group);
(11) an unsaturated $C_{2-22}$ alkyl group (for example, vinyl group, allyl group, 1-propenyl group, isopropenyl group, ethynyl group, 1-propinyl group, 2-propinyl group, 1-butynyl group, 2-butynyl group and 3-butynyl group);
(12) a $C_{6-14}$ aryl group (for example, phenyl group, 1-naphthyl group and 2-naphthyl group);
(13) a 5-membered to 14-membered heteroaryl group (for example, thienyl group, furyl group, pyridyl group, pyridazinyl group, pyrimidinyl group and pyrazinyl group);
(14) a 3-membered to 14-membered nitrogen-containing non-aromatic heterocyclic group (for example, aziridinyl group, azetidyl group, pyrrolidinyl group, pyrrolyl group, piperidyl group, piperazinyl group, imidazolyl group, pyrazolidinyl group, imidazolidinyl, morpholinyl group, imidazolinyl group, oxazolinyl group and quinuclidinyl group);
(15) a $C_{1-22}$ alkoxy group (for example, methoxy group, ethoxy group, n-propoxy group, iso-propoxy group, sec-propoxy group, n-butoxy group, iso-butoxy group, sec-butoxy group and tert-butoxy group);
(16) a $C_{6-14}$ aryloxy group (for example, phenoxy group, 1-naphthyloxy group and 2-naphthyloxy group);
(17) a $C_{7-22}$ aralkyloxy group (for example, benzyloxy group, phenethyloxy group, 3-phenylpropyloxy group, 4-phenylbutyloxy group, 1-naphthylmethyloxy group and 2-naphthylmethyloxy group);

(18) a 5-membered to 14-membered heteroaryloxy group (for example, thienyloxy group, furyloxy group, pyridinyloxy group, pyridyloxy group, pyrimidinyloxy group and pyrazinyloxy group);
(19) a $C_{2-23}$ alkanoyl group (for example, acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group and arachidoyl group);
(20) a $C_{7-15}$ aroyl group (for example, benzoyl group, 1-naphthoyl group and 2-naphthoyl group);
(21) a $C_{3-23}$ unsaturated alkanoyl group (for example, acryloyl group, propioloyl group, crotonoyl group, iso-crotonoyl group, oleoyl group and linolenoyl group);
(22) a $C_{2-23}$ alkanoyloxy group (for example, acetoxy group, propionyloxy group and acryloxy group);
(23) a $C_{2-22}$ alkoxycarbonyl group (for example, methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group and tert-butoxycarbonyl group);
(24) an unsaturated $C_{3-22}$ alkoxycarbonyl group (for example, vinyloxycarbonyl group, aryloxycarbonyl group, 1-propenyloxycarbonyl group, isopropenyloxycarbonyl group, propalgyloxycarbonyl group and 2-butynyloxycarbonyl group);
(25) a $C_{1-22}$ alkylsulfonyl group (for example, methanesulfonyl group, ethanesulfonyl group, n-propanesulfonyl group and iso-propanesulfonyl group);
(26) a $C_{6-14}$ arylsulfonyl group (for example, benzenesulfonyl group, 1 naphthalenesulfonyl group and 2-naphthalenesulfonyl group); and
(27) a $C_{1-22}$ alkylsulfonyloxy group (for example, methanesulfonyloxy group, ethanesulfonyloxy group, n-propanesulfonyloxy group and iso-propanesulfonyloxy group).

EXAMPLES

Reference Example 1

Production of Starting Material, a Macrolide Compound 11107B

One loopful of the slant culture (ISP-2 medium) of *Streptomyces* sp. Mer-11107 strain (FERM BP-7812) was inoculated into a 500 mL Erlenmeyer flask containing 50 mL of seed medium (2% of glucose, 1% of ESUSAN-MEAT manufactured by Ajinomoto Co. Ltd., 0.5% of yeast extract (manufactured by Oriental Yeast Co., Ltd.), 0.25% of sodium chloride, 0.32% of calcium carbonate, pH 6.8 before sterilization), and it was incubated at 28° C. for two days to give the first seed culture broth. 0.1 mL of the culture broth was inoculated into a 500 mL Erlenmeyer flask containing 100 mL of the same seed medium and it was incubated at 28° C. for one day to give the second seed culture broth. The second seed culture broth (800 mL) thus obtained was inoculated into a 200 L tank containing 100 L of a production medium (5% of soluble starch, 0.8% of Pharmamedia, 0.8% of gluten meal, 0.5% of yeast extract and 0.1% of calcium carbonate, pH 6.8 before sterilized) and it was cultured for five days with flowing air and stirring under the conditions of a culture temperature of 28° C., an agitation rotation of 90 rpm, a quantity of aeration of 1.0 vvm and an internal pressure of 20 kPa, to give a culture broth.

A part of the culture broth (10 L) thus obtained was extracted with 10 L of 1-butanol, and then the resulting butanol layer was evaporated to dryness, to give 100 g of crude active fraction. The crude active fraction was applied on Sephadex LH-20 (1500 mL; manufactured by Pharmacia Co. Ltd.), and eluted with tetrahydrofuran-methanol (1:1) as a solvent. An eluted fraction from 540 mL to 660 mL was concentrated to dryness, to give a residue (660 mg). The resulting residue was dissolved in a mixture of ethyl acetate and methanol (9:1; v/v) and subjected to silica gel column chromatography (WAKO GEL C-200, 50 g). The column was eluted with a mixture (2 L) consisting of n-hexane and ethyl acetate (1:9, v/v), the fractions eluted from 468 mL to 1260 mL were collected, evaporated to give 25 mg of a crude active fraction.

The obtained crude active fraction was subjected to preparative high performance liquid chromatography (HPLC) under the following preparative HPLC condition (A), and the fractions eluted at the retention time of 34 minutes were collected. After removing acetonitrile, the respective fractions were desalted by HPLC under the following preparative HPLC condition (B) to give the macrolide compound 11107B (Retention time: 37 minutes, 6 mg).

Preparative HPLC Conditions A:
Column: YMC-PACK ODS-AM SH-343-5AM, φ20 mm×250 mm (manufactured by YMC Co.)
Temperature: room temperature
Flow rate: 10 mL/min.
Detection: 240 nm
Eluent: acetonitrile/0.15% aqueous potassium dihydrogenphosphate (pH 3.5) (2:8 to 8:2, v/v, 0 to 50 min., linear gradient)
Preparative HPLC Conditions B:
Column: YMC-PACK ODS-AM SH-343-5AM, φ20 mm×250 mm (manufactured by YMC Co.)
Temperature: room temperature
Flow rate: 10 ml/min.
Detection: 240 nm
Eluent: methanol/water (2:8 to 10:0, v/v, 0 to 40 minutes, linear gradient)

Example 1

Determination of the Nucleotide Sequence of a Gene Derived from *Streptomyces* sp. A-1544 Strain (FERM BP-8446)

(1) Preparation of a DNA of *Streptomyces* sp. A-1544 Strain Chromosome

The A-1544 strain was inoculated into a medium containing 1% of glucose, 0.4% of malt extract and 1% of yeast extract and incubated at 28° C. for 3 days. The obtained culture broth was centrifuged at 3000 rpm for 10 minutes to collect the mycelia. A chromosome DNA was prepared using Blood & Cell Culture kit (QIAGEN Co.) from the mycelia.
(2) Cloning of a Partial Sequence of a DNA Encoding a Protein Having the Activity in Hydroxylating the 16-Position of the Macrolide Compound 11107

Mix primers 5Dm-3F (SEQ ID NO: 10) and 5Dm-3R (SEQ ID NO: 11) were designed and produced on reference to the amino acid sequence assumed to be that of the cytochrome P450 (CYP105D5) of *Streptmyces coelicolor* A3 (2).

In order to promote reactivity taking the fluctuation of a codon into account, mixed bases S (=C+G) and Y (=C+T) were used.

Next, these two types of primers (5Dm-3F and 5Dm-3R) and the A-1544 strain chromosome DNA obtained in the above (1) as a template, were used to run a PCR reaction. The PCR reaction was accomplished by repeating a three-stage reaction including denaturing run at 98° C. for 20 seconds, annealing run at 50° C. for 2 minutes and extension run at 68° C. for 30 seconds 35 times by using Takara LA Taq (TAKARA HOLDINGS INC.) and a PCR amplifier (T Gradient, Biometra Co.). As a result, a DNA fragment (hereinafter referred to as a DNA fragment-A1) having a size of about 500 bp was amplified. It is highly possible that this DNA fragment-A1 is a part of the DNA encoding a protein having hydroxylating activity. The DNA fragment-A1 amplified by a PCR reaction was recovered from the reaction solution by SUPREC PCR (TAKARA HOLDINGS INC.).

In order to obtain the DNA fragment-A1 in an amount enough to analyze the nucleotide sequence of the obtained DNA fragment-A1, the DNA fragment was combined with a plasmid vector pT7Blue T (Novagen Co.) by using DNA Ligation kit ver.2 (TAKARA HOLDINGS INC.) to transform E. coli JM109 strain. Thereafter, the transformed E. coli was selected using a L-broth agar media (1.0% bactotripton, 0.5% yeast extract, 0.5% NaCl, 1.5% agar) containing ampicillin (50 μg/mL), X-gal (5-bromo-4-chloro-3-indolyl-β-D-galactoside; 40 μg/mL) and IPTG (isopropyl-β-D-thiogalactopyranoside; 100 μM). The colony of the transformed E. coli thus isolated was cultured in a L-broth liquid medium (1% bactotripton, 0.5% yeast extract, 0.5% NaCl) containing ampicillin (50 μg/mL). A plasmid DNA was separated from the mycelia of the proliferated transformed E. coli and purified by using a plasmid purifying kit (QIA filter Plasmid Midi Kit, QIAGEN Co.), to obtain enough amount of the DNA fragment-A1.
(3) Analysis of the Nucleotide Sequence of the Cloned DNA Fragment-A1

The nucleotide sequence of the DNA fragment-A1 obtained in the above (2) was analyzed using a DNA nucleotide sequence analyzer (PE Biosystems 377XL) according to a dye terminator cycle sequence method. As the result of the nucleotide sequence analysis, it was clarified that the DNA fragment-A1 amplified by a PCR reaction had an exact size of 528 bp though it had been found to have a size of about 500 bp by the above measurement using electrophoresis (see the nucleotide sequence 1775 to nucleotide sequence 2302 of the sequence No. 1). Since DNA sequences corresponding to the two types of primers used in the above PCR reaction were found at both ends of the above cloned 528 bp DNA sequence, it was clarified that the DNA fragment-A1 was singularly amplified by these two types of primers (5Dm-3F and 5Dm-3R) in the above PCR reaction.
(4) Analysis of the Neighboring Region of the DNA Fragment-A1

As mentioned above, the partial sequence of the DNA encoding a protein which was derived from the A-1544 strain and had hydroxylating activity. Therefore, the amplification, cloning and sequence analysis of the nucleotide sequence in the neighboring region extending from the upstream side to downstream side of the cloned fragment were accomplished by an inverse PCR method (Cell Technology vol. 14, p. 591-593, 1995). Specifically, the A-1544 strain chromosome DNA (see the above (1)) was digested by respective restriction enzymes PstI and SalI in a H buffer solution (50 mM Tris-HCl, pH 7.5, 10 mM MgCl$_2$, 10 mM dithiothreitol and 100 mM NaCl). The obtained each DNA fragment cut by the restriction enzymes was self-circularized by using DNA Ligation Kit ver.2 (TAKARA HOLDINGS INC.).

On the other hand, primers (6PIN-2F (SEQ ID NO: 12) and 6PIN-2R (SEQ ID NO: 13) were designed and produced based on the nucleotide sequence of the DNA fragment-A1.

Next, these two primers (6PIN-2F and 6PIN-2R) and the above self-cyclized A-1544 strain chromosome DNA as a template, were used to run a PCR reaction. In the PCR reaction, the cycle of a two-stage reaction involving denaturing run at 98° C. for 20 seconds and annealing and extension run at 68° C. for 5 minutes was repeated 35 times by using Takara LA Taq (TAKARA HOLDINGS INC.) and a PCR amplifier (T Gradient, Biometra Co.).

As a result, a DNA fragment (DNA fragment-B1) about 3.5 kbp in size and a DNA fragment (DNA fragment-C1) about 2.8 kbp in size were amplified. It was highly possible that these DNA fragments were a DNA encoding a protein having hydroxylating activity and a DNA having a DNA sequence including the upstream and downstream regions of the former DNA.

The DNA fragment-B1 and the DNA fragment-C1 were recovered from the PCR amplified reaction solution by SUPREC PCR (TAKARA HOLDINGS INC.). Next, as to the obtained DNA fragment-B1 and DNA fragment-C1, in order to obtain each DNA fragment in an amount enough to analyze the nucleotide sequence of the obtained DNA fragment, a plasmid vector pT7Blue T (Novagen Co.), DNA Ligation kit ver.2 (TAKARA HOLDINGS INC.), E. coli JM109 strain and a plasmid purifying kit (QIA filter Plasmid Midi kit, QIAGEN Co.) were used in the same manner as the above (2), to obtain enough amount of each DNA fragment.
(5) Analysis of Each Nucleotide Sequence of the DNA Fragment-B1 (About 3.5 kbp in Size) and the DNA Fragment-C1 (About 2.8 kbp in Size)

Each nucleotide sequence of the DNA fragment-B1 and DNA fragment-C1 obtained in the above (4) was analyzed using a DNA nucleotide sequence analyzer (PE Biosystems 377XL) according to a dye terminator cycle sequence method. The nucleotide sequence was thus analyzed to obtain the information of the nucleotide sequence of 3793 bp shown in the sequence No. 1 from each sequence of the DNA fragment-B1 and DNA fragment-C1.

An open reading frame (ORF) in this 3793 bp was retrieved, to find that the two proteins were coded. Each amino acid sequence of these proteins was retrieved by the BLAST search, and as a result, an ORF (hereinafter referred to as psmA) coding a protein consisting of 409 amino acids having high homology to cytochrome P450 existed in the base 1322 to base 2548 of the sequence No. 1. The psmA had the highest homology (homology: 72.6%) to the amino acid sequence assumed to be that of cytochrome P450 (CYP105D5) of the Streptomyces coelicolor A3 (2) and to the amino acid sequence assumed to be that of cytochrome P450 (CYP105D4) of the Streptomyces lividans, and also had a relatively high homology (homology: 69.4%) to cytochrome P450 soy (Soy C) of Streptomyces griseus. It was considered from this fact that the psmA was highly possibly a gene coding hydroxylating enzyme of the cytochrome P-450 type.

Also, an ORF (hereinafter referred to as psmB) encoding a protein having a high homology to ferredoxin of a 3F-4S type existed just downstream (the base 2564 to base 2761 of the sequence No. 1) of the psmA. The protein encoded by the psmB consists of 66 amino acids, and had the highest homology (83.3%) to the amino acid sequence assumed to be that of ferredoxin just downstream of the amino acid sequence assumed to be that of cytochrome P450 (CYP105D5) of the Streptomyces coelicolor A3(2) and a relatively higher homology (homology: 57.6%) to ferredoxin soy (soyB) of Streptomyces griseus. Therefore, it was considered that the psmB serves to transfer electrons and codes ferredoxin participating in hydroxylation together with the psmA.

Example 2

Production of a Transformant Having the psmA and the psmB (1) Preparation of a DNA Fragment Containing Both the psmA and the psmB Derived from the A-1544 Strain A primer DM-NdeF (SEQ ID NO: 14) obtained by adding a NdeI site to the 5' terminal and a primer DM-SpeR (SEQ ID NO: 15) obtained by adding a SpeI site to the 5' terminal were designed and produced on reference to the nucleotide sequence of SEQ ID NO: 1 analyzed in Example 1. Next, these two types of primers (DM-NdeF and DM-SpeR) and the A-1544 strain chromosome DNA obtained in Example 1(1) as a template, were used to run a PCR reaction. The PCR reaction was accomplished by repeating a two-stage reaction including denaturing carried out at 98° C. for 20 seconds and annealing and elongation carried out at 68° C. for 2 minutes 30 times by using Takara LA Taq (TAKARA HOLDINGS INC.) and a PCR amplifier (T Gradient, Biometra Co.).

As a result, a DNA fragment (hereinafter referred to as a DNA fragment-D1) having a size of about 1.5 kbp and containing the psmA and the psmB was amplified. The DNA fragment-D1 was recovered from this PCR amplified reaction solution by SUPREC PCR (TAKARA HOLDINGS INC.).

(2) Architecture of a Plasmid pTC-DM pT7NS-CamAB (see WO03/087381) was digested by respective restriction enzymes NdeI and SpeI in a H buffer solution (50 mM Tris-HCl, pH 7.5, 10 mM $MgCl_2$, 10 mM dithiothreitol and 100 mM NaCl) to obtain a plasmid digested products. Similarly, the DNA fragment-D1 obtained in the above (1) was digested by respective restriction enzymes NdeI and SpeI. The obtained digested product of the DNA fragment-D1 and the plasmid digested product were coupled using DNA Ligation Kit ver.2 (TAKARA HOLDINGS INC.). This resulted in the formation of a plasmid (referred to as a plasmid PTC-DM) about 9.5 kbp in size which was an architecture of a combination of the DNA fragment-D1 containing both the psmA and the psmB therein and the plasmid pT7NS-CamAB.

(3) Preparation of *E. coli* Transforming Strain BL21 (DE3)/ pTC-DM

Using the plasmid PTC-DM prepared in the above (2), a competent cell (Novagen) of Colibacillus BL21 (DE3) was transformed. *E. coli* BL21 (DE3)/pTC-DM strain transformed by the plasmid pTC-DM was obtained.

Example 3

Conversion of ME-265 into ME-282 Represented by the Following Formulae by the *E. coli* Transformant Having the psmA and the psmB

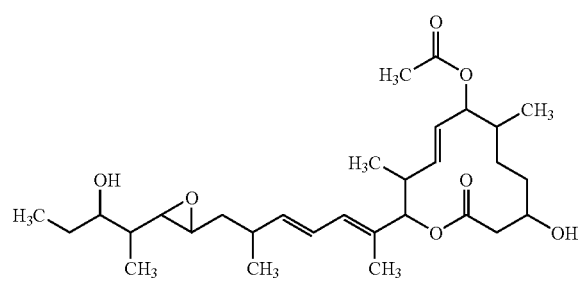

ME-265

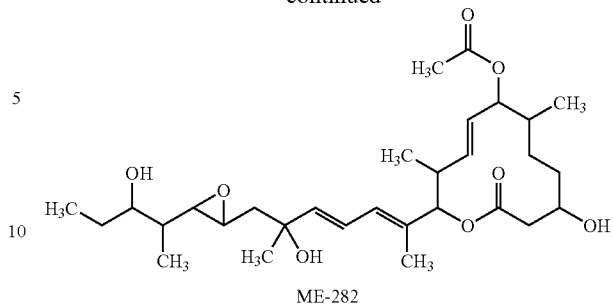

ME-282

(1) Preparation of a Transformant Reaction Solution

The transformed *E. coli* BL21(DE3)/pTC-DM strain obtained in Example 2(3) and a frozen seed of a BL21(DE3)/ pT7NS-CamAB strain were inoculated into a 15 mL test tube containing 3 mL of a L-broth medium (1.0% bactotripton, 0.5% yeast extract, 0.5% NaCl) containing 50 µg/mL of ampicillin and shake-cultured at 37° C. for 20 hours. 500 µL of the seed culture broth was inoculated into a 250 mL Erlenmeyer flask containing 50 mL of a L-broth medium (1.0% bactotripton, 0.5% yeast extract, 0.5% NaCl) containing 50 µg/mL of ampicillin and shake-cultured at 32° C. for 3 hours. Then, 50 µL of 100 mM IPTG (isopropyl-β-D-thiogalactopyranoside) and 50 µL of 80 mg/mL 5-aminolevulinic acid were successively added thereto, and the medium was shake-cultured at 32° C. for 6 hours. The obtained culture broth was centrifuged (5000 rpm, 10 minutes) to collect the mycelia. The mycelia were then suspended in 1.75 mL of a 100 mM phosphate buffer solution (pH 6.1), and 250 µL of 80% glycerol and 50 µL of 8 mg/mL ME-265 were added thereto. The conversion reaction solution thus obtained was reacted at 28° C. for 24 hours. 200 µL of the reaction solution was extracted with 1 mL of acetonitrile and the extract was subjected to HPLC to measure each amount of ME-265 and ME-282. The results are shown in Table 3.

Also, the details of the condition of HPLC are shown below.

Analyzer: Shimadzu HPLC 10Avp
Column: CAPCELL PAK C18 SG120 (φ4.6 mm×250 mm)
Mobile phase:
   45% acetonitrile (0 to 15 minutes)
   60% acetonitrile (15 to 30 minutes)
   45% acetonitrile (30 to 45 minutes)
Flow rate: 1 mL/min.
Detection: UV 240 nm
Injection capacity: 10 µL
Column temperature: 40° C.
Analyzing time: 45 minutes
Retention time:
   ME-265 24.8 minutes
   ME-282 12.7 minutes

TABLE 3

| mg/L | BL21(DE3)/pT7NS-CamAB | BL21(DE3)/pTC-DM |
|---|---|---|
| ME-265 | 143 | 0 |
| ME-282 | 0 | 130 |

(2) Isolation of ME-282 from the Transformant Reaction Solution 4 mL of water was added to 1.8 mL of the reaction solution that had been reacted for 24 hours and the reaction solution was then extracted with 8 mL of ethyl acetate once and with 4 mL of ethyl acetate twice. The ethyl acetate layers were combined, dried over anhydrous sodium sulfate and then the solvent was removed. The resulting residue was purified by thin layer chromatography (MERCK Silicagel 60 F254 0.25 mm, developing solution: hexane:ethyl acetate=1:2), to give 0.2 mg of ME-282.

$^1$H-NMR spectrum (CD$_3$OD, 500 MHz): δ ppm (integral, multiplicity, coupling constant J (Hz)):
0.87 (3H, d, J=7.0 Hz), 0.90 (3H, d, J=7.0 Hz), 0.94 (3H, t, J=7.3 Hz), 0.97 (3H, d, J=6.6 Hz), 1.21-1.26 (1H, m), 1.29-1.37 (3H, m), 1.34 (3H, s), 1.44-1.52 (2H, m), 1.60-1.64 (1H, m), 1.65 (1H, dd, J=6.2, 13.9 Hz), 1.77 (3H, d, J=1.1 Hz), 1.86 (1H, dd, J=5.4, 13.9 Hz), 1.89-1.94 (1H, m), 2.00 (3H, s), 2.43 (1H, dd, J=5.5, 13.9 Hz), 2.50-2.60 (1H, m), 2.56 (1H, dd, J=3.3, 13.9 Hz), 2.66 (1H, dd, J=2.2, 7.7 Hz), 2.89 (1H, dt, J=2.2, 6.2 Hz), 3.52 (1H, dt, J=4.8, 8.4 Hz), 3.75-3.80 (1H, m), 4.90 (1H, overlapped with D$_2$O), 5.01 (1H, d, J=10.6 Hz), 5.42 (1H, dd, J=9.2, 15.0 Hz), 6.13 (1H, d, J=10.6 Hz), 6.52 (1H, dd, J=11.0, 15.0 Hz).

As a result, a peak estimated as that of ME-282 was not observed in the case of the *E. coli* BL21(DE3)/pT7NS-CamAB strain used as a control, whereas ME-265 was almost consumed and a peak estimated as that of ME-282 was obtained in the case of the BL21(DE3)/pTC-DM strain containing the psmA and psmB. This fact suggests that the psmA and the psmB participate in the conversion of ME-265 into ME-282.

Example 4

Conversion of the Macrolide Compound 11107B into the Macrolide Compound 11107D by the *E. coli* Transformant Having the psmA and the psmB (1) Preparation of a Transformant Reaction Solution A test using the macrolide compound 11107B as a substrate was made in the same manner as Example 3. The transformed *E. coli* BL21(DE3)/pTC-DM strain obtained in Example 2(3) and a frozen seed of a BL21(DE3)/pT7NS-CamAB strain were inoculated into a 15 mL test tube containing 3 mL of a L-broth medium (1.0% bactotripton, 0.5% yeast extract, 0.5% NaCl) containing 50 μg/mL of ampicillin and shake-cultured at 30° C. for 20 hours. 500 μL of the seed culture broth was inoculated into a 250 mL Erlenmeyer flask containing 50 mL of a L-broth medium (1.0% bactotripton, 0.5% yeast extract, 0.5% NaCl) containing 50 μg/mL of ampicillin and shake-cultured at 28° C. for 5 hours. Then, 50 μL of 100 mM IPTG (isopropyl-β-D-thiogalactopyranoside) and 50 μL of 80 mg/mL 5-aminolevulinic acid were successively added and the medium was shake-cultured at 25° C. for 20 hours. The obtained culture broth was centrifuged (5000 rpm, 10 minutes) to collect the mycelia. The mycelia were then suspended in 1.75 mL of a 100 mM phosphate buffer solution (pH 6.1), and 250 μl of 80% glycerol and 50 μL of 40 mg/mL 11107B were added thereto. The conversion reaction solution thus obtained was reacted at 28° C. for 24 hours. 200 μL of the reaction solution was extracted with 1 mL of acetonitrile and the extract was subjected to HPLC to measure each amount of the macrolide compound 11107B and the macrolide compound 11107D. The results are shown in Table 4. Also, the details of the condition of HPLC are shown below.
Analyzer: Shimadzu HPLC 10Avp
Column: CAPCELL PAK C18 SG120 (φ4.6 mm×250 mm)
Mobile phase:
  35% acetonitrile (0 to 10 minutes)
  35% to 65% acetonitrile (10 to 12 minutes)
  35% acetonitrile (12 to 15 minutes)
  35% acetonitrile (15 to 20 minutes)
Flow rate: 1 mL/min.
Detection: UV 240 nm
Injection capacity: 10 μL
Column temperature: 40° C.
Analyzing time: 20 minutes
Retention time:
  11107B 14.3 minutes
  11107D 7.9 minutes

TABLE 4

| mg/L | BL21(DE3)/pT7NS-CamAB | BL21(DE3)/pTC-DM |
|---|---|---|
| 11107B | 636 | 619 |
| 11107D | 0 | 71 |

(2) Isolation of the Macrolide Compound 11107D from the Transformant Reaction Solution 4 mL of water was added to 1.8 mL of the reaction solution that had been reacted for 24 hours and the mixture was then extracted with 8 mL of ethyl acetate once and with 4 mL of ethyl acetate twice. The ethyl acetate layers were combined, dried over anhydrous sodium sulfate and the solvent was removed. The resulting residue was purified by thin layer chromatography (MERCK Silicagel 60 F254 0.25 mm, developing solution: ethyl acetate) to obtain 0.1 mg of 11107D.

$^1$H-NMR spectrum (CD$_3$OD, 500 MHz): δ ppm (integral, multiplicity, coupling constant J (Hz)):
0.87 (3H, d, J=7.0 Hz), 0.88 (3H, d, J=7.0 Hz), 0.93 (3H, t, J=7.0 Hz), 1.18 (3H, s), 1.18-1.69 (8H, m), 1.33 (3H, s), 1.77 (3H, d, J=1.1 Hz), 1.82-1.90 (1H, m), 2.05 (3H, s), 2.49-2.60 (3H, m), 2.66 (1H, dd, J=2.2, 8.2 Hz), 2.89 (1H, dt, J=2.4, 5.7 Hz), 3.52 (1H, dt, J=4.8, 8.3 Hz), 3.73-3.82 (1H, m), 5.04 (1H, d, J=9.8 Hz), 5.05 (1H, d, J=10.6 Hz), 5.56 (1H, dd, J=9.8, 15.2 Hz), 5.70 (1H, dd, J=9.8, 15.2 Hz), 5.86 (1H, d, J=15.2 Hz), 6.3 (1H, d, J=10.8 Hz), 6.52 (1H, dd, J=10.8, 15.2 Hz).

As a result, a peak estimated as that of the macrolide compound 11107D was not observed in the case of the *E. coli* BL21(DE3)/pT7NS-CamAB strain used as a control, whereas a peak estimated as that of the macrolide compound 11107D was obtained in the case of the BL21(DE3)/pTC-DM strain containing the psmA and psmB. This fact suggests that the psmA and the psmB participate in the conversion of macrolide compound 11107B into the macrolide compound 11107D.

Example 5

Conversion Test Using an A-1544 Self-Cloning Strain (1) Preparation of a DNA Fragment Containing Both the psmA and the psmB Derived from the A-1544 Strain A primer DM-BglF (SEQ ID NO: 16) obtained by adding a BglII site to the 5' terminal and a primer DM-BglR (SEQ ID NO: 17) obtained by adding a BglII site to the 5' terminal were designed and produced on reference to the nucleotide sequence of SEQ ID NO: 1 analyzed in Example 1.

Next, these two types of primers (DM-BglF and DM-BglR) and the A-1544 strain chromosome DNA obtained in Example 1(1) as a template, were used to run a PCR reaction. The PCR reaction was accomplished by repeating a three-stage reaction including denaturing carried out at 98° C. for 20 seconds, annealing carried out at 63° C. for 30 seconds and elongation carried out at 68° C. for 4 minutes 30 times by using Takara LA Taq (TAKARA HOLDINGS INC.) and a PCR amplifier (T Gradient, Biometra Co.).

As a result, a DNA fragment (hereinafter referred to as a DNA fragment-E1) having a size of about 3.5 kbp and containing the psmA and the psmB was amplified. This PCR amplified reaction solution was subjected to agarose gel electrophoresis to fractionate. The above DNA fragment-E1 about 3.5 kbp in size was cut out of the agarose gel and recovered by SUPREC 01 (TAKARA HOLDINGS INC.).

(2) Architecture of a Plasmid pIJDMG pIJ702 was digested by a restriction enzyme BglII in a H buffer solution (50 mM Tris-HCl, pH 7.5, 10 mM $MgCl_2$, 10 mM dithiothreitol and 100 mM NaCl) to obtain a plasmid digested products. Similarly, the DNA fragment-E1 obtained in the above (1) was digested by a restriction enzyme BglII. The obtained digested product of the DNA fragment-E1 and the plasmid-digested product were bound using DNA Ligation Kit ver.2 (TAKARA HOLDINGS INC.). The resulted in the formation of a plasmid (referred to as a plasmid pIJDMG) about 8.5 kbp in size which was an architecture of a combination of the DNA fragment-E1 containing both the psmA and the psmB therein and the plasmid pIJ702.

(3) Preparation of a Self-Cloning Strain A-1544/pIJDMG Strain

Using the plasmid pIJDMG prepared in the above (2), an A-1544 strain was transformed according to the method described in Genetic Manipulation of *Streptomyces*: A Laboratory Manual. John Innes Foundation, Norwich, 1985. An A-1544/pIJDMG strain was thus obtained by transformation using the plasmid pIJDMG.

Example 6

Conversion of 11107B into 11107D by a Self-Cloning Strain

The transformed A-1544/pIJDMG strain obtained in Example 5(3), A-1544/pIJ702 strain and a frozen seed of the original A-1544 strain were inoculated into a 250 mL Erlenmeyer flask containing 50 mL of a SMN medium (Stabilose 2%, glucose 2%, ESUSAN-MEAT 2%, yeast extract 0.5%, NaCl 0.25%, $CaCO_3$ 0.32%, pH 7.4) containing 25 µg/mL of thiostrepton, and shake-cultured at 28° C. for 48 hours (seed culture, no addition of thiostrepton to the A-1544 strain). 0.5mL of the obtained seed culture broth was inoculated into a 250 mL Erlenmeyer flask containing 50 mL of a SMN medium containing 25 µg/mL of thiostrepton and shake-cultured at 28° C. for 72 hours (no addition of thiostrepton to the A-1544 strain). The obtained culture broth was dispensed in 2 mL portions, and 100 µL of a 1M phosphate buffer solution (pH 6.5) and 50 µL of 40 mg/mL of 11107B were added thereto. The conversion culture broth thus obtained was reacted at 28° C. for 12 hours. 200 µL of the reaction solution was extracted with 1 mL of acetonitrile and the extract was subjected to HPLC to measure each amount of 11107B and 11107D. The results are shown in Table 5. Also, the details of the condition of HPLC are shown below.

Analyzer: Shimadzu HPLC 10Avp
Column: CAPCELL PAK C18 SG120 (φ4.6 mm×250 mm)
Mobile phase:
    35% acetonitrile (0 to 10 minutes)
    35% to 65% acetonitrile (10 to 12 minutes)
    65% acetonitrile (12 to 15 minutes)
    35% acetonitrile (15 to 20 minutes)
Flow rate: 1 mL/min.
Detection: UV 240 nm
Injection capacity: 10 µL
Column temperature: 40° C.
Analyzing time: 20 minutes
Retention time:
    11107B 14.3 minutes
    11107D 7.9 minutes

TABLE 5

| mg/L | A-1544 strain | A-1544/pIJ702 strain | A-1544/pIJDMG strain |
|---|---|---|---|
| 11107B | 496 | 651 | 14 |
| 11107D | 196 | 0 | 535 |

As a result, the A-1544/pIJDMG strain obtained by transformation of the plasmid containing the psmA and the psmB exhibited conversion activity about 2.7 times that of the original A-1544 strain by a reaction run for 12 hours. This fact suggests that the self-cloning of the psmA and psmB contributes to the conversion of the macrolide compound 11107B into the macrolide compound 11107D.

Example 7

Determination of the Nucleotide Sequence of a Gene Derived from *Streptomyces* sp. Mer-11107 Strain (FERM BP-7812)

(1) Preparation of a DNA of *Streptomyces* sp. Mer-11107 Strain Chromosome

The Mer-11107 strain was inoculated into a medium containing 1% of glucose, 0.4% of malt extract and 1% of yeast extract and cultured at 28° C. for 3 days. The obtained culture broth was centrifuged at 3000 rpm for 10 minutes to collect the mycelia. A chromosome DNA was prepared using Blood & Cell Culture kit (QIAGEN Co.) from the mycelia.

(2) Cloning of a Partial Sequence of a DNA Encoding a Protein Having the Activity in Hydroxylating the 16-Position of the Macrolide Compound 11107

Mix primers 5Dm-3F (SEQ ID NO: 10) and 5D-1R (SEQ ID NO: 18) were designed and produced on reference to the amino acid sequence estimated as that of the cytochrome P450 (CYP105D5) of *Streptmyces coelicolor* A3(2).

In order to promote reactivity taking the fluctuation of a codon into account, mixed bases S (=C+G) and Y (=C+T) were used.

Next, these two types of primers (5Dm-3F and 5D-1R) and the Mer-11107 strain chromosome DNA obtained in the above (1) as a template, were used to run a PCR reaction. The PCR reaction was accomplished by repeating a three-stage reaction including denaturing carried out at 98° C. for 20 seconds, annealing carried out at 50° C. for 2 minutes and elongation carried out at 68° C. for 30 seconds 35 times by using Takara LA Taq (TAKARA HOLDINGS INC.) and a PCR amplifier (T Gradient, Biometra Co.). As a result, a DNA fragment (hereinafter referred to as a DNA fragment-A2) having a size of about 300 bp was amplified. It is highly possible that the DNA fragment-A2 is a part of the DNA encoding a protein having hydroxylating activity. The DNA fragment-A2 amplified by a PCR reaction was recovered from the reaction solution by SUPREC PCR (TAKARA HOLDINGS INC.).

In order to obtain the DNA fragment-A2 in an amount enough to analyze the nucleotide sequence of the obtained DNA fragment-A2, the DNA fragment was bound with a plasmid vector pT7Blue T (Novagen Co.) by using DNA Ligation kit ver.2 (TAKARA HOLDINGS INC.) to transform E. coli JM109 strain. Thereafter, the transformed E. coli was selected using a L-broth agar media (1.0% bactotripton, 0.5% yeast extract, 0.5% NaCl, 1.5% agar) containing ampicillin (50 μg/mL), X-gal (5-bromo-4-chloro-3-indolyl-β-D-galactoside; 40 μg/mL) and IPTG (isopropyl-β-D-thiogalactopyranoside; 100 μM). The colony of the transformed E. coli thus isolated was cultured in a L-broth liquid medium (1% bactotripton, 0.5% yeast extract, 0.5% NaCl) containing ampicillin (50 μg/mL). A plasmid DNA was separated from the mycelia of the proliferated transformed E. coli and purified by using a plasmid purifying kit (QIA filter Plasmid Midi Kit, QIAGEN Co.), to obtain enough amount of the DNA fragment-A2.

(3) Analysis of the Nucleotide Sequence of the Cloned DNA Fragment-A2

The nucleotide sequence of the DNA fragment-A2 obtained in the above (2) was analyzed using a DNA nucleotide sequence analyzer (PE Biosystems 377XL) according to a dye terminator cycle sequence method. As the result of the nucleotide sequence analysis, it was clarified that the DNA fragment-A2 amplified by a PCR reaction had an exact size of 325 by though it had been found to have a size of about 300 by the above measurement using electrophoresis (see the nucleotide sequence 837 to nucleotide sequence 1161 of SEQ ID NO: 4). Since DNA sequences corresponding to the two types of primers used in the above PCR reaction were found at both ends of the above cloned 325 by DNA sequence, it was clarified that the DNA fragment-A2 was specifically amplified by these two types of primers (5Dm-3F and 5D-1R) in the above PCR reaction.

(4) Analysis of the Neighboring Region of the DNA Fragment-A2

As mentioned above, the partial sequence of the DNA encoding a protein having the hydroxylating activity derived from the Mer-11107 strain was determined. Therefore, the amplification, cloning and sequence analysis of the nucleotide sequence in the neighboring region extending from the upstream side to downstream side of the cloned fragment were accomplished by an inverse PCR method (Cell Technology vol. 14, p. 591-593, 1995). Specifically, the Mer-11107 strain chromosome DNA (seethe above (1)) was digested by a restriction enzyme BamHI in a K buffer solution (50 mM Tris-HCl, pH 8.5, 10 mM MgCl$_2$, 1 mM dithiothreitol and 100 mM KCl) and by a restriction enzyme SalI in a H buffer solution (50 mM Tris-HCl, pH 7.5, 10 mM MgCl$_2$, 1 mM dithiothreitol and 100 mM NaCl) respectively. The obtained each DNA fragment cut by the restriction enzymes was self-circularized using DNA Ligation Kit ver.2 (TAKARA HOLDINGS INC.).

On the other hand, primers (7PIN-2F (SEQ ID NO: 19) and 6PIN-2R (SEQ ID NO: 13) were designed and produced based on the nucleotide sequence of the DNA fragment-A2.

Next, these two primers (7PIN-2F and 6PIN-2R) and the above self-circularized Mer-11107 strain chromosome DNA as a template, were used to run a PCR reaction. In the PCR reaction, the cycle of a two-stage reaction involving denaturing carried out at 98° C. for 20 seconds and annealing and elongation carried out at 68° C. for 5 minutes was repeated 35 times by using Takara LA Taq (TAKARA HOLDINGS INC.) and a PCR amplifier (T Gradient, Biometra Co.).

As a result, a DNA fragment (DNA fragment-B2) about 1.3 kbp in size and a DNA fragment (DNA fragment-C2) about 1.4 kbp in size were amplified. It was highly possible that these DNA fragments were respectively a DNA encoding a protein having hydroxylating activity and a DNA having a DNA sequence including those in the upstream and downstream regions of the former DNA.

The DNA fragment-B2 and the DNA fragment-C2 were recovered from the PCR amplified reaction solution by SUPREC PCR (TAKARA HOLDINGS INC.). Next, as to the obtained DNA fragment-B2 and DNA fragment-C2, in order to obtain each DNA fragment in an amount enough to analyze the nucleotide sequence of the obtained DNA fragment, a plasmid vector pT7Blue T (Novagen Co.), DNA Ligation kit ver.2 (TAKARA HOLDINGS INC.), E. coli JM109 strain and a plasmid purifying kit (QIA filter Plasmid Midi Kit, QIAGEN Co.) were used in the same manner as the above (2), to obtain enough amount of each DNA fragment.

(5) Analysis of Each Nucleotide Sequence of the DNA Fragment-B2 (About 1.3 kbp in Size) and the DNA Fragment-C2 (About 1.4 kbp in Size)

Each nucleotide sequence of the DNA fragment-B2 and DNA fragment-C2 obtained in the above (4) was analyzed using a DNA nucleotide sequence analyzer (PE Biosystems 377XL) according to a dye terminator cycle sequence method. The nucleotide sequence was thus analyzed to obtain the information of the nucleotide sequence of 2329 by shown in SEQ ID NO: 4 from each sequence of the DNA fragment-B2 and DNA fragment-C2.

An open reading frame (ORF) in this 2329 by was retrieved, to find that the two kinds of protein were coded. Each amino acid sequence of these proteins was retrieved by the BLAST search, and as a result, an ORF (hereinafter referred to as bpmA) encoding a protein consisting of 395 amino acids having high homology to cytochrome P450 existed in the base 420 to base 1604 of SEQ ID NO: 4. The bpmA had the highest homology (homology: 67.4%) to the amino acid sequence of the psmA isolated from the A-1544 strain and also had a relatively high homology (homology: 64.8%) to cytochrome P450 soy (Soy C) of Streptmyces griseus. It was considered from this fact that the bpmA highly possibly encoded hydroxyllating enzyme of the cytochrome P-450 type.

Also, an ORF (hereinafter referred to as bpmB) encoding a protein having a high homology to ferredoxin of a 3Fe-4S type that existed just downstream (the base 1643 to base 1834 of SEQ ID NO: 4) of the bpmA. The protein encoded by the bpmB consisted of 64 amino acids, and had the highest homology (81.0%) to the amino acid sequence of the psmB isolated from the A-1544 strain and a relatively higher homology (homology: 76.2%) to the amino acid sequence assumed to be that of ferredoxin just downstream of the amino acid sequence assumed to be cytochrome P450 (CYP105D5) of Streptmyces coelicolor A3(2). Therefore, it was considered that the bpmB served to transfer electrons and participated in hydroxylation together with the bpmA.

Example 8

Production of a Transformant Having the bpmA and the bpmB (1) Preparation of a DNA Fragment Containing Both the bpmA and the bpmB Derived from the Mer-11107 Strain A primer 07-NdeF (SEQ ID NO: 20) obtained by adding a NdeI site to the 5' terminal and a primer 07-SpeR (SEQ ID NO: 21) obtained by adding a SPeI site to the 5' terminal were designed and produced on reference to the nucleotide sequence of SEQ ID NO: 4 analyzed in Example 7. Next, these two types of primers (07-NdeF and 07-SpeR) and the Mer-11107 strain chromosome DNA obtained in Example 7(1) as a template, were used to run a PCR reaction. The PCR reaction was accomplished by repeating a two-stage reaction including denaturing carried out at 98° C. for 20 seconds and annealing and elongation carried out at 68° C. for 2 minutes 30 times by using Takara LA Taq (TAKARA HOLDINGS INC.) and a PCR amplifier (T Gradient, Biometra Co.).

As a result, a DNA fragment (hereinafter referred to as a DNA fragment-D2) having a size of about 1.5 kbp and containing the psmA and the psmB was amplified. The DNA fragment-D2 was recovered from the PCR amplified reaction solution by SUPREC PCR (TAKARA HOLDINGS INC.).

(2) Architecture of a Plasmid pTC-D07 pT7NS-CamAB (see WO03/087381) was digested by respective restriction enzymes NdeI and SpeI in a H buffer solution (50 mM Tris-HCl, pH 7.5, 10 mM MgCl$_2$, 1 mM dithiothreitol and 100 mM NaCl) to obtain a plasmid digested products. Similarly, the DNA fragment-D2 obtained in the above (1) was digested by respective restriction enzymes NdeI and SpeI. The obtained digested product of the DNA fragment-D2 and the plasmid digested product were bound using DNA Ligation Kit ver.2 (TAKARA HOLDINGS INC.). Thereby, a plasmid (referred to as a plasmid pTC-D07) about 9.5 kbp in size which was an architecture of a combination of the DNA fragment-D2 containing both the bpmA and the bpmB therein and the plasmid pT7NS-CamAB was formed.

(3) Preparation of *E. coli* Transforming Strain BL21 (DE3)/pTC-D07

Using the plasmid pTC-D07 prepared in the above (2), a competent cell (Novagen) of Colibacillus BL21 (DE3) was transformed. Thereby, *E. coli* BL21 (DE3)/pTC-D07 strain transformed by the plasmid pTC-D07 was obtained.

Example 9

Conversion of the Macrolide Compound 11107B into the 11107D by the *E. coli* Transformant Having the bpmA and the bpmB The transformed *E. coli* BL21(DE3)/pTC-D07 strain obtained in Example 8(3) and a frozen seed of a BL21(DE3)/pT7NS-CamAB strain were inoculated into a 15 mL test tube containing 3 mL of a L-broth medium (1.0% bactotripton, 0.5% yeast extract, 0.5% NaCl) containing 50 μg/mL of ampicillin and shake-cultured at 37° C. for 20 hours. 500 μL of the seed culture broth was inoculated into a 250 mL Erlenmeyer flask containing 50 mL of a L-broth medium (1.0% bactotripton, 0.5% yeast extract, 0.5% NaCl) containing 50 μg/mL of ampicillin and shake-cultured at 32° C. for 4 hours. Then, 50 μL of 100 mM IPTG (isopropyl-β-D-thiogalactopyranoside) and 50 μL of 80 mg/mL 5-aminolevulinic acid were successively added and the medium was shake-cultured at 32° C. for 5 hours. The obtained culture broth was centrifuged (5000 rpm, 10 minutes) to collect the mycelia. The mycelia were then suspended in 1.75 mL of a 100 mM phosphate buffer solution (pH 6.1), to which were then added 250 μL of 80% glycerol and 12.5 μL of 40 mg/mL macrolide compound 11107B. The conversion reaction solution obtained in this manner was reacted at 28° C. for 24 hours. 400 μL of the reaction solution was extracted with 600 μL of methanol and the extract was subjected to HPLC to measure each amount of macrolide compounds 11107B and 11107D. The results are shown in Table 6.

Also, the details of the condition of HPLC are shown below.
Analyzer: Shimadzu HPLC 10Avp
Column: Develosil ODS UG-3 (φ4.6 mm×250 mm 3 μm)
Mobile phase:
    45% to 55% methanol (0 to 5 minutes)
    55% methanol (5 to 13 minutes)
    55% to 70% methanol (13 to 17 minutes)
    70% methanol (17 to 21 minutes)
    45% methanol (21 to 25 minutes)
Flow rate: 1.2 mL/min.
Detection: UV 240 nm
Injection capacity: 5 μL
Column temperature: 40° C.
Analyzing time: 25 minutes
Retention time:
    11107B 12.2 minutes
    11107D 4.2 minutes

TABLE 6

| mg/L | BL21(DE3)/pT7NS-CamAB | BL21(DE3)/pTC-D07 |
|---|---|---|
| 11107B | 162 | 156 |
| 11107D | 0.00 | 0.78 |

As a result, the peak of the macrolide compound 11107D was not observed in the case of the *E. coli* BL21(DE3)/pT7NS-CamAB strain used as a control, whereas the peak of the macrolide compound 11107D was obtained in the case of the BL21(DE3)/pTC-D07 strain containing the psmA and psmB. This fact suggests that the bpmA and the bpmB participate in the conversion of the macrolide compound 11107B into the macrolide compound 11107D.

Example 10

Determination of the Nucleotide Sequence of a Gene Derived from the A-1560 Strain (FERM BP-10102)

(1) Preparation of a DNA of the A-1560 Strain Chromosome

The A-1560 strain was inoculated into a medium containing 1% of glucose, 0.4% of malt extract and 1% of yeast extract and cultured at 28° C. for 3 days. The obtained culture broth was centrifuged at 3000 rpm for 10 minutes to collect the mycelia. A chromosome DNA was prepared using Blood & Cell Culture kit (QIAGEN Co.) from the mycelia.

(2) Cloning of a Partial Sequence of a DNA Encoding a Protein Having the Activity in Hydroxylating the 16-Position of the Macrolide Compound 11107

Mix primers (5Dm-3F (SEQ ID NO: 10) and 5Dm-2R (SEQ ID NO: 22) were designed and produced on reference to the amino acid sequence estimated as that of the cytochrome P450 (CYP105D5) of *Streptmyces coelicolor* A3(2).

In order to promote reactivity taking the fluctuation of a codon into account, mixed bases S (=C+G) and Y (=C+T) were used.

Next, these two types of primers (5Dm-3F and 5Dm-2R) and the A-1560 strain chromosome DNA obtained in the above (1) as a template, were used to run a PCR reaction. The PCR reaction was accomplished by repeating a three-stage reaction including denaturing carried out at 98° C. for 20 seconds, annealing carried out at 50° C. for 2 minutes and elongation carried out at 68° C. for 30 seconds 35 times by using Takara LA Taq (TAKARA HOLDINGS INC.) and a PCR amplifier (T Gradient, Biometra Co.). As a result, a DNA fragment (hereinafter referred to as a DNA fragment-A3) having a size of about 750 bp was amplified. It is highly possible that this DNA fragment-A3 is a part of the DNA encoding a protein having hydroxylating activity. The DNA fragment-A3 amplified by a PCR reaction was recovered from the reaction solution by SUPREC PCR (TAKARA HOLDINGS INC.).

In order to obtain the DNA fragment-A3 in an amount enough to analyze the nucleotide sequence of the obtained DNA fragment-A3, the DNA fragment-A3 was bound with a plasmid vector pT7Blue T (Novagen Co.) by using DNA Ligation kit ver.2 (TAKARA HOLDINGS INC.) to transform E. coli JM109 strain (Stratagene Co.). Thereafter, the transformed E. coli was selected using a L-broth agar media (1.0% bactotripton, 0.5% yeast extract, 0.5% NaCl, 1.5% agar) containing ampicillin (50 µg/mL), X-gal (5-bromo-4-chloro-3-indolyl-β-D-galactoside; 40 µg/mL) and IPTG (isopropyl-β-D-thiogalactopyranoside; 100 µM). The colony of the transformed E. coli thus isolated was cultured in a L-broth liquid medium (1% bactotripton, 0.5% yeast extract, 0.5% NaCl) containing ampicillin (50 µg/mL). A plasmid DNA was separated from the mycelia of the proliferated transformed E. coli and purified by using a plasmid purifying kit (QIA filter Plasmid Midi Kit, QIAGEN Co.), to obtain enough amount of the DNA fragment-A3.

(3) Analysis of the Nucleotide Sequence of the Cloned DNA Fragment-A3

The nucleotide sequence of the DNA fragment-A3 obtained in the above (2) was analyzed using a DNA nucleotide sequence analyzer (PE Biosystems 377XL) according to a dye terminator cycle sequence method. As the result of the nucleotide sequence analysis, it was clarified that the DNA fragment-A3 amplified by a PCR reaction had an exact size of 741 by though it had been found to have a size of about 750 by the above measurement using electrophoresis (see the nucleotide sequence 616 to nucleotide sequence 1356 of SEQ ID NO: 7). Since DNA sequences corresponding to the two types of primers used in the above PCR reaction were found at both ends of the above cloned 741 by DNA sequence, it was clarified that the DNA fragment-A3 was singularly amplified by these two types of primers (5Dm-3F and 5Dm-2R) in the above PCR reaction.

(4) Analysis of the Neighboring Region of the DNA Fragment-A3

As mentioned above, the partial sequence of the DNA encoding a protein having hydroxylating activity derived from the A-1560 strain was determined. Therefore, the amplification, cloning and sequence analysis of the nucleotide sequence in the neighboring region extending from the upstream side to downstream side of the cloned fragment were accomplished by an inverse PCR method (Cell Technology vol. 14, p. 591-593, 1995). Specifically, the A-1560 strain chromosome DNA (see the above (1)) was digested by a restriction enzyme BamHI in a K buffer solution (50 mM Tris-HCl, pH 8.5, 10 mM $MgCl_2$, 1 mM dithiothreitol and 100 mM KCl), by a restriction enzyme KpnI in a L buffer solution (10 mM Tris-HCl, pH 7.5, 10 mM $MgCl_2$ and 1 mM dithiothreitol) and by a restriction enzyme SalI in a H buffer solution (50 mM Tris-HCl, pH 7.5, 10 mM $MgCl_2$, 1 mM dithiothreitol and 100 mM NaCl) respectively. The obtained each DNA fragment cut by the restriction enzymes was self-circularized using DNA Ligation Kit ver.2 (TAKARA HOLDINGS INC.).

On the other hand, primers (5PIN-2F (SEQ ID NO: 23) and 6PIN-2R (SEQ ID NO: 13)) were designed and produced based on the nucleotide sequence of the DNA fragment-A3.

Next, these two primers (5PIN-2F and 6PIN-2R) and the above self-circularized A-1560 strain chromosome DNA as a template, were used to run a PCR reaction. In the PCR reaction, the cycle of a two-stage reaction involving denaturing carried out at 98° C. for 20 seconds and annealing and elongation carried out at 68° C. for 5 minutes was repeated 35 times by using Takara LA Taq (TAKARA HOLDINGS INC.) and PCR amplifier (T Gradient, Biometra Co.).

As a result, a DNA fragment (DNA fragment-B3) about 4.5 kbp in size, a DNA fragment (DNA fragment-C3) about 3.0 kbp in size and a DNA fragment (DNA fragment-D3) about 1.7 kbp in size were amplified. It was highly possible that these DNA fragments were a DNA encoding a protein having hydroxylating activity and a DNA having a DNA sequence including those in the upstream and downstream regions of the former DNA.

The DNA fragment-B3, the DNA fragment-C3 and the DNA fragment-D3 were recovered from the PCR amplified reaction solution by SUPREC PCR (TAKARA HOLDINGS INC.). Next, as to the obtained DNA fragment-B3, DNA fragment-C3 and DNA fragment-D3, in order to obtain each DNA fragment in an amount enough to analyze the nucleotide sequence of the obtained DNA fragment, a plasmid vector pT7Blue T (Novagen Co.), DNA Ligation kit ver.2 (TAKARA HOLDINGS INC.), E. coli JM109 strain and a plasmid purifying kit (QIA filter Plasmid Midi Kit, QIAGEN Co.) were used in the same manner as the above (2), to obtain enough amount of each DNA fragment.

(5) Analysis of Each Nucleotide Sequence of the DNA Fragment-B3 (About 4.5 kbp in Size), the DNA Fragment-C3 (About 3.0 kbp in Size) and the DNA Fragment-D3 (About 1.7 kbp in Size)

Each nucleotide sequence of the DNA fragment-B3, DNA fragment-C3 and DNA fragment-D3 obtained in the above (4) was analyzed using a DNA nucleotide sequence analyzer (PE Biosystems 377XL) according to a dye terminator cycle sequence method. The nucleotide sequence was thus analyzed to obtain the information of the nucleotide sequence of 1860 by shown in SEQ ID NO: 7 from each sequence of the DNA fragment-B3, DNA fragment-C3 and DNA fragment-D3.

An open reading frame (ORF) in this 1860 by was retrieved, to find that the two kinds of protein were encoded. Each amino acid sequence of these proteins was retrieved by the BLAST search, and as a result, an ORF (hereinafter referred to as tpmA) encoding a protein consisting of 404 amino acids having high homology to cytochrome P450 existed in the base 172 to base 1383 of SEQ ID NO: 7. The tpmA had the highest homology (homology: 77.4%) to the amino acid sequence assumed to be that of cytochrome P450 (CYP105D5) of Streptmyces coelicolor A3(2) and also a high homology (homology: 76.6%) to the amino acid sequence of the psmA isolated from the A-1544 strain. It was considered from this fact that the tpmA was highly possibly a gene encoding hydroxylating enzyme of the cytochrome P-450 type.

Also, an ORF (hereinafter referred to as tpmB) encoding a protein having a high homology to ferredoxin of a 3Fe-4S type existed just downstream (the base 1399 to base 1593 of SEQ ID NO: 7) of the tpmA. The protein encoded by the tpmB consisted of 65 amino acids, and had the highest homology (81.0%) to the amino acid sequence of the psmB isolated from the A-1544 strain and also a high homology (homology: 82.5%) to the amino acid sequence assumed to be that of ferredoxin just downstream of the amino acid sequence assumed to be cytochrome P450 (CYP105D5) of Streptmyces coelicolor A3 (2). Therefore, it was considered that the tpmB served to transfer electrons and coded ferredoxin participating in hydroxylation together with the tpmA.

Example 11

Production of a Transformant Having the tpmA and the tpmB (1) Preparation of a DNA Fragment Containing Both the tpmA and the tpmB Derived from the A-1560 Strain A primer tpm-NdeF (SEQ ID NO: 24) obtained by adding a NdeI site to the 5' terminal and a primer tpm-SpeR (SEQ ID NO: 25) obtained by adding a SpeI site to the 5' terminal were designed and produced on reference to the nucleotide sequence of the SEQ ID NO: 7 analyzed in Example 10. Next, these two types of primers (tpm-NdeF and tpm-SpeR) and the A-1560 strain chromosome DNA obtained in Example 10(1) as a template, were used to run a PCR reaction. The PCR reaction was accomplished by repeating a two-stage reaction including denaturing carried at 98° C. for 20 seconds and annealing and elongation carried out at 68° C. for 2 minutes 30 times by using Takara LA Taq (TAKARA HOLDINGS INC.) and a PCR amplifier (T Gradient, Biometra Co.).

As a result, a DNA fragment (hereinafter referred to as a DNA fragment-E3) having a size of about 1.5 kbp and containing the tpmA and the tpmB was amplified. The DNA fragment-E3 was recovered from this PCR amplified reaction solution by SUPREC PCR (TAKARA HOLDINGS INC.).

(2) Architecture of a Plasmid pTC-tpmAB pT7NS-CamAB (see WO03/087381) was digested by respective restriction enzymes NdeI and SpeI in a H buffer solution (50 mM Tris-HCl, pH 7.5, 10 mM $MgCl_2$, 1 mM dithiothreitol and 100 mM NaCl) to obtain plasmid digested products. Similarly, the DNA fragment-E3 obtained in the above (1) was digested by respective restriction enzymes NdeI and SpeI. The obtained digested product of the DNA fragment-E3 and the plasmid digested product were bound using DNA Ligation Kit ver.2 (TAKARA HOLDINGS INC.). Thereby, a plasmid (referred to as a plasmid pTC-tpmAB) about 9.5 kbp in size which was an architecture of a combination of the DNA fragment-E3 containing both the tpmA and the tpmB therein and the plasmid pT7NS-CamAB was formed.

(3) Preparation of *E. coli* Transforming Strain BL21 (DE3)/pTC-tpmAB

Using the plasmid pTC-tpmAB prepared in Example 11(2), a competent cell (Novagen) of Colibacillus BL21 (DE3) was transformed, to give *E. coli* BL21 (DE3)/pTC-tpmAB strain transformed by the plasmid pTC-tpmAB.

Example 12

Conversion of the 11107B into the 11107D by the *E. coli* Transformant Having the tpmA and the tpmB The transformed *E. coli* BL21(DE3)/pTC-tpmAB strain obtained in the above (3) and a frozen seed of a BL21(DE3)/pT7NS-CamAB strain were inoculated into a 15 mL test tube containing 3 mL of a L-broth medium (1.0% bactotripton, 0.5% yeast extract, 0.5% NaCl) containing 50 μg/mL of ampicillin and shake-cultured at 37° C. for 20 hours. 500 μL of the seed culture broth was inoculated into a 250 mL Erlenmeyer flask containing 50 mL of a L-broth medium (1.0% bactotripton, 0.5% yeast extract, 0.5% NaCl) containing 50 μg/mL of ampicillin and shake-cultured at 32° C. for 4 hours. Then, 50 μL of 100 mM IPTG (isopropyl-β-D-thiogalactopyranoside) and 50 μL of 80 mg/mL 5-aminolevulinic acid were successively added thereto, and the medium was shake-cultured at 32° C. for 5 hours. The obtained culture broth was centrifuged (5000 rpm, 10 minutes) to collect the mycelia. The mycelia were suspended in 1.75 mL of a 100 mM phosphate buffer solution (pH 6.1), and 250 μL of 80% glycerol and 12.5 μL of 40 mg/mL macrolide compound 11107B were added thereto. The conversion reaction solution obtained in this manner was reacted at 28° C. for 24 hours. 400 μL of the reaction solution was extracted with 600 μL of methanol and the extract was subjected to HPLC to measure each amount of macrolide compounds 11107B and 11107D. The results are shown in Table 7. Also, the details of the condition of HPLC are shown below.

Analyzer: Shimadzu HPLC 10Avp

Column: Develosil ODS UG-3 (φ4.6 mm×250 mm 3 μm)

Mobile phase:
  45% to 55% methanol (0 to 5 minutes)
  55% methanol (5 to 13 minutes)
  55% to 70% methanol (13 to 17 minutes)
  70% methanol (17 to 21 minutes)
  45% methanol (21 to 25 minutes)

Flow rate: 1.2 mL/min.

Detection: UV 240 nm

Injection capacity: 5 μL

Column temperature: 40° C.

Analyzing time: 25 minutes

Retention time:
  11107B 12.2 minutes
  11107D 4.2 minutes

TABLE 7

| mg/L | BL21(DE3)/pT7NS-CamAB | BL21(DE3)/pTC-tpmAB |
|---|---|---|
| 11107B | 141 | 128 |
| 11107D | 0 | 18 |

As a result, the peak of the macrolide compound 11107D was not observed in the case of the *E. coli* BL21(DE3)/pT7NS-CamAB strain used as a control, whereas the peak of 11107D was obtained in the case of the BL21(DE3)/pTC-tpmAB strain containing the tpmA and tpmB. This fact suggests that the tpmA and the tpmB participate in the conversion of 11107B into 11107D.

Example 13

Conversion of 11107H into 11107CB Represented by the Following Formulae by a Self-Cloning Strain

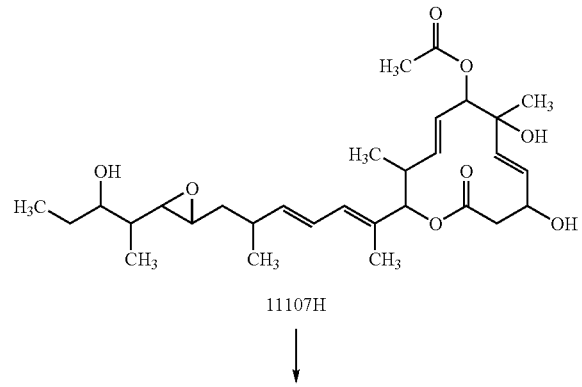

11107H

↓

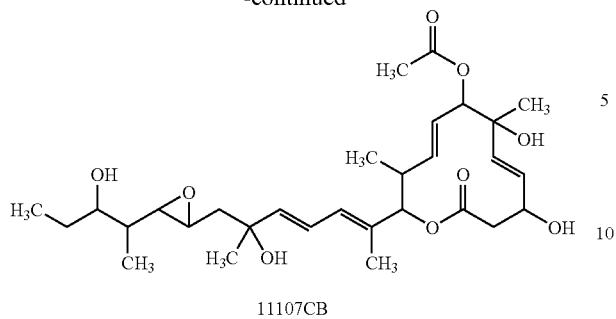

11107CB (1) Preparation of a Transformant Reaction Solution

A medium containing 2.0% of soluble starch, 2.0% of glucose, 2.0% of a soybean meal (Honen Soypro), 0.5% of yeast extract and 0.32% of $CaCO_3$ and having a pH of 7.4 was prepared. A 250 mL Erlenmeyer flask was charged with 25 mL of the medium, which was then sterilized under heating at 121° C. for 20 minutes and thiostrepton was added to the medium such that its final concentration was 25 mg/L. Then, 1% of an A-1544/pIJDMG strain from frozen seed was inoculated to culture the seed at 28° C. and 220 rpm for 3 days. 1% of the seed culture broth was added in a medium having the same composition to carry out main culturing at 28° C. and 220 rpm for 2 days. After the main culturing was finished, mycelia were collected from the culture broth by centrifugation and suspended in 20 mL of phosphate buffer solution having a pH of 6.5. The substrate 11107H (100 g/L DMSO solution) was added in this mycelia suspended solution such that its final concentration was 2000 mg/L to run a conversion reaction at 28° C. and 220 rpm for 16 hours.

(2) Isolation of a Macrolide Compound 11107CB from a Transformant Reaction Solution Mycelia were isolated from a conversion reaction solution (in an amount corresponding to 6 flasks) obtained from the same operation, by centrifugation and the centrifuged supernatant was extracted with the equal amount of ethyl acetate twice. The extract was concentrated and then the residue was purified by thin layer chromatography (MERCK Silicagel 60 F254' 0.5 mm, developing solution: toluene:acetone=1:1), to obtain 119.5 mg of 11107CB.

$^1$H-NMR spectrum ($CD_3OD$, 500 MHz): δ ppm (integral, multiplicity, coupling constant J (Hz)):

0.81 (3H, d, J=6.7 Hz), 0.89 (3H, d, J=7.0), 0.94 (3H, t, J=7.4 Hz), 1.25 (3H, s), 1.30-1.20 (1H, m), 1.33 (3H, s), 1.55-1.40 (2H, m), 1.65 (1H, dd, J=6.3, 14.0 Hz), 1.75 (3H, s), 1.88 (1H, dd, J=5.4, 14.0 Hz), 2.07 (3H, s), 2.68-2.40 (4H, m), 2.89 (1H, m), 3.51 (1H, m), 4.51 (1H, m), 4.97 (1H, d, J=8.6 Hz), 4.99 (1H, d, J=9.3 Hz), 5.30 (1H, dd, J=9.7, 15.2 Hz), 5.52 (1H, dd, J=9.4, 15.2 Hz), 5.58 (1H, dd, J=1.9, 15.5 Hz), 5.78 (1H, dd, J=2.8, 15.5 Hz), 5.85 (1H, d, J=15.3 Hz), 6.07 (1H, d, J=11.0 Hz), 6.51 (1H, dd, J=11.0, 15.3 Hz)

Example 14

Conversion of 11107L into 11107CG Represented by the Following Formulae Respectively by a Self-Cloning Strain

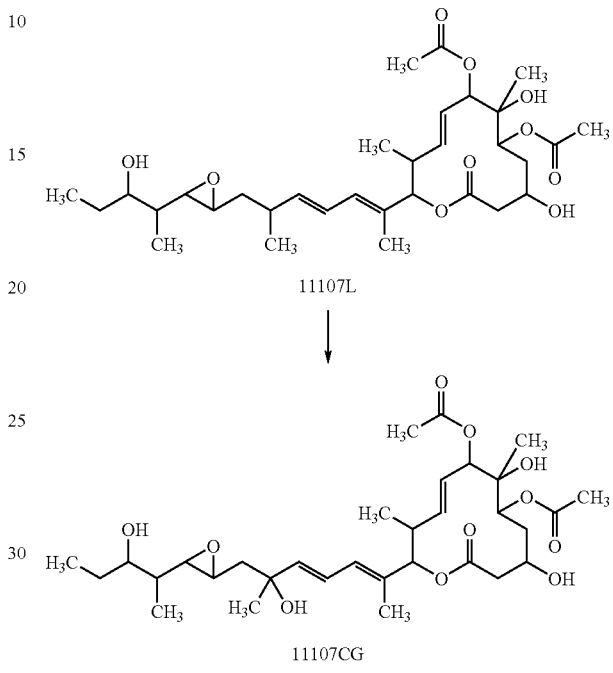

(1) Preparation of a Transformant Reaction Solution

A medium containing 2.0% of soluble starch, 2.0% of glucose, 2.0% of a soybean meal (Honen Soypro), 0.5% of yeast extract and 0.32% of $CaCO_3$ and having a pH of 7.4 was prepared. A 250 mL Erlenmeyer flask was charged with 25 mL of the medium, which was then sterilized under heating at 121° C. for 20 minutes and thiostrepton was added to the medium such that its final concentration was 25 mg/L. Then, 1% of an A-1544/pIJDMG strain from frozen stock was inoculated to cultivate the seed culture at 28° C. and 220 rpm for 3 days. 1% of this seed culture broth was added in a medium having the same composition to carry out main cultivation at 28° C. and 220 rpm for 2 days. After the main cultivation was finished, mycelia were collected from the culture broth by centrifugation and suspended in 20 mL of phosphate buffer solution having a pH of 6.5. The substrate 11107L (100 g/L DMSO solution) was added to this mycelia suspension solution such that its final concentration was 1600 mg/L to run a conversion reaction at 28° C. and 220 rpm for 16 hours.

(2) Isolation of a Macrolide Compound 11107CG from a Transformant Reaction Solution Mycelia were isolated from the conversion reaction solution by centrifugation and the centrifuged supernatant was extracted with the equivalent amount of ethyl acetate twice. The extract layers were concentrated and then the residue was purified by thin layer chromatography (MERCK Silicagel 60 F254' 0.25 mm, developing solution: toluene:acetone=1:1), to obtain 25 mg of 11107CG.

ESI-MS m/z 633 (M+Na)+
¹H-NMR spectrum (CD₃OD, 500 MHz): δ ppm ((integral, multiplicity, coupling constant J (Hz)):
0.88 (3H, d, J=6.7 Hz), 0.90 (3H, d, J=7.0 Hz), 0.94 (3H, d, J=7.4 Hz), 1.18 (3H, s), 1.30-1.20 (1H, m), 1.34, (3H, s), 1.56-1.40 (2H, m), 1.66 (1H, dd, J=6.2, 14.0 Hz), 1.79-0.169 (2H, m), 1.81 (3H, d, J=1.0 Hz), 1.86 (1H, dd, J=5.4, 14.0 Hz), 2.05 (3H, s), 2.08 (3H, s), 2.52 (1H, dd, J=4.2, 15.2 Hz), 2.64-2.55 (1H, m), 2.67 (1H, dd, J=2.2, 7.9 Hz), 2.78 (1H, dd, J=3.0, 15.2 Hz), 2.90 (1H, dt, J=2.2, 5.6 Hz), 3.52 (1H, dt, J=4.4, 8.8 Hz), 3.75 (1H, m), 4.98 (1H, dd, J=2.8, 11.3 Hz), 5.08 (1H, d, J=9.7 Hz), 5.13 (1H, d, J=9.6 Hz), 5.61 (1H, dd, J=9.9, 15.2 Hz), 5.75 (1H, dd, J=9.7, 15.2 Hz), 5.88 (1H, d, J=15.3 Hz), 6.13 (1H, d, J=11.0 Hz), 6.54 (1H, dd, J=11.0, 15.3 Hz)

INDUSTRIAL APPLICABILITY

A 12-membered macrolide compound which has hydroxyl group at the 16-position and is excellent in antitumor activity and stability in an aqueous solution can be produced efficiently by using a transformant obtained by transformation using a plasmid carrying the DNA of the present invention.

The invention claimed is:

1. A DNA participating in biological transformation of a macrolide compound (hereinafter referred to as a macrolide compound 11107B) represented by the formula (I):

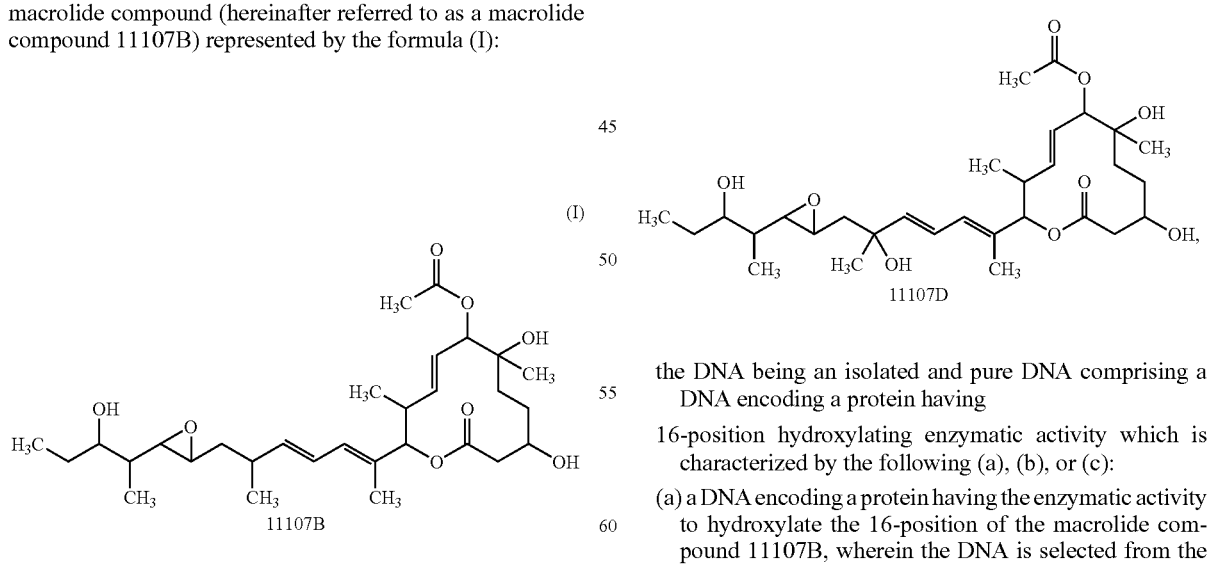

into a 16-position hydroxy macrolide compound represented by the formula (II):

the DNA being an isolated and pure DNA comprising a DNA encoding a protein having 16-position hydroxylating enzymatic activity which is characterized by the following (a), (b), or (c):

(a) a DNA encoding a protein having the enzymatic activity to hydroxylate the 16-position of the macrolide compound 11107B, wherein the DNA is selected from the group consisting of (1) a continuous nucleotide sequence from base 1322 to base 2548 of SEQ ID NO: 1; (2) a continuous nucleotide sequence from base 420 to base 1604 of SEQ ID NO: 4; and (3) a continuous nucleotide sequence from base 172 to base 1383 of SEQ ID NO: 7;

(b) a DNA which has a nucleotide sequence having 90% or more identity over the full length sequence with the DNA described in (a);

(c) a DNA encoding a protein having the same amino acid sequence as the protein encoded by the DNA described in (a) or (b) though it does not have 90% or more identity with the DNA described in (a) because of the degeneracy of a gene codon.

2. A self-replicative or integrating replicative recombinant plasmid carrying the DNA as claimed in claim 1.

3. An isolated transformant obtained by transformation of the recombinant plasmid of claim 2.

4. The DNA according to claim 1, wherein the DNA comprises bases 1322-2548 of SEQ ID NO: 1.

5. The DNA according to claim 1, wherein the DNA encodes a polypeptide comprising SEQ ID NO: 2.

6. The DNA according to claim 1, wherein the DNA consists of bases 1322-2548 of SEQ ID NO: 1.

7. The DNA according to claim 1, wherein the DNA encodes a polypeptide consisting of SEQ ID NO: 2.

8. The DNA according to claim 1, wherein said identity in (b) and (c) of claim 1 is 95% or more.

9. A DNA comprising
   (a) a DNA encoding a protein, wherein the DNA is selected from the group consisting of (1) a continuous nucleotide sequence from base 1322 to base 2548 of SEQ ID NO: 1; (2) a continuous nucleotide sequence from base 420 to base 1604 of SEQ ID NO: 4; and a continuous nucleotide sequence from base 172 to base 1383 of SEQ ID NO: 7;
   (b) a DNA which has a nucleotide sequence having 90% or more identity over the full length sequence with the DNA described in (a); or
   (c) a DNA encoding a protein having the same amino acid sequence as the protein encoded by the DNA described in (a) or (b) though it does not have 90% or more identity with the DNA described in (a) because of the degeneracy of a gene codon.

10. The DNA according to claim 9, wherein said identity in (b) and (c) of claim 9 is 95% or more.

* * * * *